(12) United States Patent
Moore et al.

(10) Patent No.: US 8,487,005 B2
(45) Date of Patent: *Jul. 16, 2013

(54) TRANEXAMIC ACID FORMULATIONS

(75) Inventors: Keith A. Moore, Loveland, OH (US);
Ralph A. Heasley, Webster Grove, MO (US); Jeffrey S. Greiwe, Ft. Thomas, KY (US); John W. Facemire, Douglasville, GA (US); Jason D. Modest, Minneapolis, MN (US)

(73) Assignee: Ferring B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/620,148

(22) Filed: Sep. 14, 2012

(65) Prior Publication Data
US 2013/0012584 A1   Jan. 10, 2013

Related U.S. Application Data

(63) Continuation of application No. 12/228,489, filed on Aug. 13, 2008, now Pat. No. 8,273,795, which is a continuation of application No. 11/072,194, filed on Mar. 4, 2005, now abandoned.

(60) Provisional application No. 60/592,885, filed on Jul. 30, 2004, provisional application No. 60/550,113, filed on Mar. 4, 2004.

(51) Int. Cl.
*A61K 31/19* (2006.01)
*A61K 31/195* (2006.01)

(52) U.S. Cl.
USPC ................................. 514/574; 514/561

(58) Field of Classification Search
USPC .................................. 514/574, 561
See application file for complete search history.

(56) References Cited

U.S. PATENT DOCUMENTS

| | | |
|---|---|---|
| 4,171,377 A | 10/1979 | Green et al. |
| 4,258,030 A | 3/1981 | Sasaki et al. |
| 4,465,662 A | 8/1984 | Sato et al. |
| 4,483,867 A | 11/1984 | Svahn et al. |
| 4,711,782 A | 12/1987 | Okada |
| 5,068,110 A | 11/1991 | Fawzi et al. |
| 5,229,135 A | 7/1993 | Phillippon et al. |
| 5,242,337 A | 9/1993 | Greenwood et al. |
| 5,271,945 A | 12/1993 | Yoshioka |
| 5,506,264 A | 4/1996 | Fujimura et al. |
| 5,575,987 A | 11/1996 | Kamei et al. |
| 5,622,657 A | 4/1997 | Takada et al. |
| 5,650,174 A | 7/1997 | Muhammad et al. |
| 5,723,269 A | 3/1998 | Akagi et al. |

(Continued)

FOREIGN PATENT DOCUMENTS

| | | |
|---|---|---|
| CA | 2086565 | 7/1994 |
| EP | 0 998 916 | 5/2000 |

(Continued)

OTHER PUBLICATIONS

Aulton et al., Pharmaceutics the Science of Dosage and Design, Chapters 1 (pp. 1-11), 5 (pp. 62-80) and 18 (pp. 304-321) (1988).

(Continued)

*Primary Examiner* — Savitha Rao
(74) *Attorney, Agent, or Firm* — Fish & Richardson P.C.

(57) ABSTRACT

Disclosed are modified release oral tranexamic acid formulations and methods of treatment therewith.

41 Claims, 3 Drawing Sheets

U.S. PATENT DOCUMENTS

| | | | |
|---|---|---|---|
| 5,738,874 | A | 4/1998 | Conte et al. |
| 5,747,030 | A | 5/1998 | Kohnert et al. |
| 5,807,583 | A | 9/1998 | Kristensen et al. |
| 5,858,411 | A | 1/1999 | Nakagami et al. |
| 5,874,463 | A | 2/1999 | Ancira |
| 5,877,175 | A | 3/1999 | Sargent et al. |
| 5,897,910 | A | 4/1999 | Rosenberg |
| 6,051,253 | A | 4/2000 | Zettler |
| 6,066,339 | A | 5/2000 | Stark et al. |
| 6,113,943 | A | 9/2000 | Okada et al. |
| 6,120,802 | A | 9/2000 | Breitenbach |
| 6,159,502 | A | 12/2000 | Russell Jones |
| 6,197,331 | B1 | 3/2001 | Lerner et al. |
| 6,274,171 | B1 | 8/2001 | Sherman et al. |
| 6,300,369 | B1 | 10/2001 | Ancira |
| 6,328,979 | B1 | 12/2001 | Ywmashita |
| 6,433,215 | B1 | 8/2002 | Jung |
| 6,548,084 | B2 | 4/2003 | Leonard et al. |
| 6,551,616 | B1 | 4/2003 | Notario et al. |
| 7,192,608 | B2 | 3/2007 | Ochiai |
| 7,235,530 | B2 | 6/2007 | Blair et al. |
| 7,273,624 | B2 | 9/2007 | Rosenberg et al. |
| 7,351,740 | B2 | 4/2008 | Zerangue |
| 2002/0132855 | A1 | 9/2002 | Nelson et al. |
| 2003/0133985 | A1 | 7/2003 | Louie-Helm et al. |
| 2003/0190353 | A1 | 10/2003 | Oosterbaan et al. |
| 2004/0006021 | A1 | 1/2004 | Rojkjaer et al. |
| 2004/0052843 | A1 | 3/2004 | Lerner et al. |
| 2004/0096499 | A1 | 5/2004 | Vaya |
| 2004/0258753 | A1 | 12/2004 | Demeester |
| 2005/0025825 | A1 | 2/2005 | Heasley et al. |
| 2005/0059742 | A1 | 3/2005 | Jabbour et al. |
| 2005/0244495 | A1 | 11/2005 | Moore et al. |
| 2005/0245614 | A1 | 11/2005 | Moore et al. |
| 2005/0267014 | A1 | 12/2005 | Rojkaer et al. |
| 2006/0003006 | A1 | 1/2006 | Remon |
| 2006/0018933 | A1 | 1/2006 | Vaya et al. |
| 2006/0018934 | A1 | 1/2006 | Vaya |
| 2006/0127476 | A1 | 6/2006 | Heasley et al. |
| 2006/0193914 | A1 | 8/2006 | Asworth |
| 2006/0287258 | A1 | 12/2006 | Jabbour et al. |
| 2007/0020335 | A1 | 1/2007 | Chen et al. |
| 2007/0027210 | A1 | 2/2007 | Zerangue et al. |
| 2008/0193414 | A1 | 8/2008 | Proudfoot |
| 2008/0280981 | A1 | 11/2008 | Moore et al. |
| 2009/0017114 | A1 | 1/2009 | Moore et al. |
| 2009/0214644 | A1 | 8/2009 | Heasley et al. |
| 2009/0215898 | A1 | 8/2009 | Moore et al. |
| 2010/0143468 | A1 | 6/2010 | Moore et al. |
| 2010/0280117 | A1 | 11/2010 | Patrick et al. |

FOREIGN PATENT DOCUMENTS

| | | |
|---|---|---|
| EP | 0 923 934 | 8/2003 |
| EP | 1 586 315 | 10/2005 |
| GB | 2073019 | 10/1981 |
| JP | 57059847 | 4/1982 |
| JP | 4-243825 | 8/1992 |
| JP | 06219942 | 8/1994 |
| JP | 07206660 | 8/1995 |
| JP | 9077726 | 3/1997 |
| JP | 09124878 | 5/1997 |
| JP | 09255542 | 9/1997 |
| JP | 10-017497 | 1/1998 |
| JP | 2000-159674 | 6/2000 |
| JP | 2001-163774 | 6/2001 |
| JP | 2002-265358 | 9/2002 |
| WO | WO94/15904 | 7/1994 |
| WO | WO96/19200 | 6/1996 |
| WO | WO2004/028503 | 4/2004 |
| WO | WO2004/060364 | 7/2004 |
| WO | WO2005/011650 | 2/2005 |
| WO | WO2006/023000 | 3/2006 |
| WO | WO2006/023001 | 3/2006 |
| WO | WO2008/111096 | 9/2008 |
| WO | WO2008/148798 | 12/2008 |

OTHER PUBLICATIONS

Bradshaw et al., Answer to Complaint for Patent Infringment and Counterclaims, dated Feb. 15, 2013, 16pp.

Dollery et al., Therapeutic Drugs, Second Edition, pp. T150-T154 (1999).

Lethaby et al., Antifibrinolytics for Heavy Menstrual Bleeding, Cochrane Database of Systematic Reviews, Issue 4, 2002, (61pp.).

Rounds et al., Answer, Affirmative Defenses and Counter-Claims to Complaint for Patent Infringement, dated Feb. 28, 2013, 19pp.

1996 Physician's Desk Reference, $50^{th}$ Edition, on Tranexamic acid (Cyklokapron), pp. 1950-1951.

A brochure containing information relating to Tab. Trexamic and Tab. Trexamic-M (Reference A14), submitted to USPTO on Jul. 6, 2010.

Abbott, J.A., et al. "Quality of Life should be Considered the Primary outcome for Measuring success of endometrial Ablation", J.Am. Assoc. Gynecol. Laparosc., 2003, 10(4); 491-495.

ACOG Practice Bulletin; "Management of anovulatory bleeding, 2000, No. 14", International J. Gynecology obstetrics 72(2001) 263-271.

Alexander, D.A. et al, "Randomized trial comparing hysterectomy with endometrial ablation of dysfunctional bleeding; psychiatric and psychosocial aspects,"BMJ, 1996, 312:280-284.

Andersch, Bjorn et al, "An Objective Evaluation of Flurbiprofen and Tranexamic Acid in the Treatment of Idiopathic Menorrhagia," *Acta Obstet Gynecol Scand*, 1988; 67: 645-648.

Anderson L., et al, "Special Considerations with Regard to the Dosage of Tranexamic Acid in patients with Chronic Renal Diseases," *Urological Research* 6, 83-88 (1978).

Anderson, I. et al, "Role of Urokinase and Tissue Activator in Sustaining Bleeding and the Management Thereof with EACA and AMCA," *Annals N.Y. Acad. Sci.*, 146, p. 642-658. (1968).

Ansari, Tariq Mahmood, et al, "Spectrophotometric Determination of Tranexamic Acid in Pharmaceutical Bulk and Dosage Forms", Analytical Sciences, Sep. 2005, vol. 21, p. 1133-35.

Apgar, Barbara S. et al, "Treatment of Menorrhagia", American Family Physician, Jun. 15, 2007, vol. 75, No. 12, p. 1813-1819.

Article: "Health-Related Quality of Life and Activity limitation-Eight States", 1995, MMWR, 1998, 47(7), 134-140.

Astedt, B., "Clinical Pharmacaology of Tranexamic Acid", Scand J. Gastroenterol 1987, 22 (suppl 137), 22-25.

Bekassy, Z. et al., "Treatment with the Fibrinolytic Inhibitor Tranexamic Acid—Risk for Thrombosis?" *Ada Obstet Gynecol Scand*, 1990; 69: 353-354.

Ben-Tovim, D.I., et al., "The Influence of Age and Weight on Women's Body Attitudes as measured by the Body Attitudes Questionnaire (BAQ)" j. Psychosomatic Res., 1994, 38(5) 477-481.

Berntorp, "No increased Risk of Venous Thrombosis in Women Taking Tranexamic Acid," Thromb Haemostat., 2001; 86: 714-5.

Bonnar J. et al., "Treatment of Menorrhagia during menstruation: randomized controlled trial of ethamsylate, mefenamic acid, and tranexamic acid," *BMJ* 1996; 313: 579-82.

Bravo et al In-Vitro Studies of Diclofenac Sodium Controlled-release Biopolymeric Hydrophilic Matrices Journal Pharmacy and Pharmaceutical Science 5(3), p. 213-219, 2002.

British National Formulary, ed., Section 2.11 Antibrincyltic drugs and Haemostactics, p. 123, submitted to USPTO on May 6, 2010.

Busija, L. et al, "Magnitude and meaningfulness of change in SF-36 scores in four types of orthopedic surgery", Health and Quality of Life Outcomes, 2008, 6:55.

Callendar S., et al, "Treatment of Menorrhagia with Tranexamic Acid. A Double-blind Trial" *British Medical Journal*, 1970, 4, 214-216.

Cameron, Medical Management of Menorrhagia, Current Obstetrics and Gynecology, 1992, 2, 136-140.

Carlson, K. J., et al, "The Maine Women's health Study: I. Outcomes of hysterectomy", Obstet. Gynecol, 1994; 83:556-65.

CECMED Product Characteristics; Rottapharms S.L.; solution for injection, IV, IV Infusion, oral, 5mg/ml. vial Aug. 18, 2009, 8 pp.

Cella, D., May Clinic Proc. vol. 77(4), Apr. 2002, 384-392.

Chauhan, Cynthia, "Denouement: A Patient-Reported Observation," *Value in Health*, 2007: 10: suppl 2, 1098-3015/07/S146.

Committee for Proprietary Medicinal Products (CPMP) Opinion Following an Article 10 Referral, CYKLO-f, Jul. 2000.

Consultation Document: Arm 30, Request to Reclassify a Product from Pom to P, Safeguarding public health, Medicines and Healthcare products Regulatory Agency, Feb. 7, 2007.

Consumer Medicine Information leaflet, "CYKLOKAPRON Tranexamic acid tablets and solution for injection", Pfizer Australia Pty Ltd 2010, 4 pp.

Cooper, Jay, MD et al, "A randomized multicenter trial of safety and efficacy of the Nova Sure System in the treatment of Menorrhagia," *J Am Assoc Gynecol Laparosc*, 2002; 9(4); 418-428.

Cooper, K. et al, "Five-year follow-up of women randomized to medical management or transcervical resection of the endometrium for heavy menstrual loss: clinical and quality of life outcomes," *Br. J. Obste. Gynaecol.*, 2001; 108: 1222-1228.

Cooper, K., et al, "Comparison of microwave endometrial ablation and transcervical resection of the endometrium for treatment of heave menstrual loss; a randomized trial," *The Lancet*, 1999; 354.

Cooper, K.G. et al, "A randomized comparison of medical and hysterscopic management in women consulting a gynecologist for treatment of heavy menstrual loss," *British Journal of Obstetrics and Gynaecology*, 1997; 104:1360.

Cooper, Kevin G. et al, "Two-year follow up of women randomized to medical management or transcervical resection of the endometrium for heavy menstrual loss; clinical and quality of life outcomes," *British Journal of Obstetrics and Gynaecology*, Mar. 1999; 106: 258-265.

Cote I., et al., "Work Loss Associated With Increased Menstrual Loss in the United States", Obstet Gynecol, 2002; 100; 683-7.

Coulter A., et al. "Quality of Life and Patent Satisfaction Following Treatment for Menorrhagia"Family Practice, 1994:11(4); 394-401.

Coulter, Angela et al, "Sharing decisions with patients: Is the information good enough?" *BJM*, 1999; 318: 318-322.

CPMP Opinion, *The European Agency for the Evaluation of Medical Products Evaluation of Medicines for Human Use*, Jul. 27, 2000—CPMP/902/00.

Crosignani, Pier Giorgio, MD et al, "Endometrial resection versus vaginal hysterectomy for menorrhagia: Long-term clinical and quality-of-life Outcomes," Obstet Synecol, 1997, 177:95-101.

Crosignani, Pier Giorgio, MD et al, "Levonorgestrel-Releasing Intrauterine Device versus Hysteroscopic Endometrial Resection in the Treatment of Dysfunctional Uterine Bleeding," *Obstet Gynecol*, 1997, 90: No. 2.

Crotts, G et al., Development of an enteric coating formulation and process for tablets primarily composed of a highly water soluble organic acid: European. J. Pharmaceutics and Biopharmaceutics 51, (2001), 71-76.

Cyklokapron, Tranexamic Acid Tablets, Consumer Medicine Information. 3 pp. (2001).

Cyklokapron® Package Insert, Pharmacia & Upjohn, revised Oct. 2000, 6 pages.

Cyklokapron® Package Insert, Pharmacia Canada, Inc., Misissauga, Ontario, (Nov. 2002).

Cyklokapron Tablets—Summary of Product Characteristics (SPC), http://emc.medicines.org.uk/medicine/16512/SPC/Cycklokapron+Tablets/ downloaded on Aug. 26, 2009.

Cyklokapron, Tranexamic acid tablets and injection, Pharmacia, 2001.

Cyklokapron, Tranexamic acid Tablets and Tranexamic acid Injection, Product Description, p. 1-6 (2005).

Cyklokapron, Tranexamic acid Tablets and Tranexamic acid Injection, Antifibrinolytic agent, Pharmacia & Upjohn, p. 1-6 (2005).

Cyklokapron, Tranexamic acid tablets BP and Tranexamic acid injection BP, Product Monograph, Pfizer Canada Inc. Sep. 10, 2003.

Cyklokapron, Tranexamic Acid, Data Sheet, http:/www.medsafe.govt.nz/Profs/datasheet/c/Cyckloprontabinj.htm downloaded Aug. 26, 2009, 7 pp.

De Souza, S.S., et al., "Hemoglobin levels predict quality of life in women with heavy menstrual bleeding", Arch. Gynecol. Obstet., Aug. 20, 2009.

Demers et al., "Gynaecological and Obstetric Management of Women with Inherited Bleeding Disorders," JOGC, No. 163, Jul. 2005, pp. 707-718.

Deyo, R.A., et al, "Reproducibility and Responsiveness of Health Status Measures; Statistics and Strategies for Evaluation", Controlled Clinical Trials: 1991, 12, 142S-158S.

Dockeray, C. et al, "The fibrinolytic enzyme system in normal menstruation and excessive uterine bleeding and the effect of Tranexamic Acid," Eur. J. Obstet. Gynecol. Reprod. Biol., 24 (1987) 309-318.

Dow Chemical Co., METHOCEL as a Binding Agent for Tablet Production by Wet Granulation (14 pages) (1985).

Dow Chemical Co., Formulating for Controlled Release with METHOCEL Cellulose Ethers (35 pages) (1987).

Dowd N., et al, Pharmacokinetics of Tranexamic Acid during Cardiopulmonary Bypass, *Anesthesiology*, 2002; 97: 390-99.

Dr. Giangrande, P.L.F., "Tranexamic Acid", http://www.Medicine ox.ac.uk/ohc/tranexam.htm, p. 1 downloaded Nov. 4, 2004.

Draft Guidance: Patient-reported Outcome Measures: Use in Medical Product Development to Support Labeling Claims, Feb. 2006.

Dubber, AHC., et al, "Amino Methyl Cyclohexane Carboxylic Acid (AMCHA), A New Synthetic Fibrinolytic Inhibitor," *British J Haemat*, 1965; 11:237.

Dubber, AHC., et al, "Some Properties of the antifibrinolytic active isomer of Amino-Methylclohexane Carboxylic Acid," *The Lancet*, 1964; 2:1317-9.

Dueck, A., et al, "Meeting on the FDA Draft Guidance on Patient-Reported Outcomes," *Value in Health*, 2007: 10:supppl 2, S64-S65.

Dunn, C.J., et al., "Tranexamic Acid; A Review of its Use in Surgery and Other Indications", Drugs, Jun. 1999 57 (6); 1005-1032.

Edlund, M., et al, "Reduction of menstrual blood loss in women suffering from idiopathic menorrhagia with a novel antifibrinolytic drug (Kabi2161)," *British Journal of Obstetrics and Gynecology*, 1995; 102; 913-917.

EMEA, "Committee for Proprietary Medicinal products Opinion Following an Article 10 Referral CYKLO-1 (Tranexamic acid)", EMEA Jul. 27, 2000, pp. 1-8.

Eriksson O., et al, "Pharmacokinetics of Tranexamic Acid after Intravenous Administration to Normal Volunteers," Europ. J. Clin. Pharmacol. 7, 375-380 (1974).

EuroQol Group, "Euro-Qol—a new facility for the measurement of health-related quality of life", health Policy, 16 (1990) 199-208.

FDA Guidance for Industry: Patient-Reported Outcome Measures: Use in Medical Product Development to Support Labelling Claims; Feb. 2006.

FDA Guidance for Industry: Patient-Reported Outcome Measures: Use in Medical Product Development to Support Labelling Claims; Dec. 2009.

Ferguson, R.J., et al, "Use of the Reliable Change Index to evaluate Clinial significance in SF-36 Outcomes", Quality of Life Research, 11:509-6, 2002.

Flood, E.M., et al., "Psychometric evaluation of the Osteoporosis Patient Treatment Satisfaction Questionnaire (OPSAT-Q), a novel measure to assess satisfaction with bisphosphonate treatment in postmenopausal women" Health and Quality of Life Outcomes 2006, 4: 42.

Florence et al Novel Oral Drug Formulation, Their Potential in Modulating Adverse Effects Drug Safety, 10(3) p. 233-266, 1994.

Fraser, I. S., "Estimating Menstrual Blood Loss in women with Normal and Excessive Menstrual Fluid Volume," *Obset Gynecol*, 2001; 98: 806-14.

Frost, M., et al, "What is Sufficient Evidence for the Reliability and Validity of Patient-Reported Outcome Measures?" *Value in Health*, 2007; 10:suppl 2, S94-S105.

Garratt, A.M. et al, "SF 36 health survey questionnaire: II: Responsiveness to changes in health status in four common clinical conditions," *Quality in Health Care*, 1994; 3: 186-192.

Garratt, A.M. et al, "The SF 36 health survey questionnaire: an outcome measure suitable for routine use within the NHS?" *British Medical Journal*, 1993; 306.

Gath, D., et al, "Psychiatric disorder and gynaecological symptoms in middle aged women; a community survey," *British Medical Journal*, 1987; 294: 213.

Gleeson, N.C. et al, The effect of tranexamic acid on measured menstrual loss and endometrial fibinolytic enzymes in dysfunctional uterine bleeding, *Acta Obstet Gynecol Scand* 1994; 73: 274-277.

Gorgen, H., et al., "Use of the Levonorgestrel-IUS in the treatment of menorrhagia: assessment of quality of life in Turkish users", Arch Gynecol Obstet, pub. Online Nov. 19, 2008.

Greenberg Quinlan Rosner Research Inc., "Survey of Women Who Experience Heavy Menstrual Bleeding" for Nation Women's Health Resource Center, Nov. 15, 2005.

Gumpel, J.M. et al., "Self-administered Clinical Questionnaire for outpatients", British Medical Journal, 174, 209-212. (1974).

Guyatt, G.H., MD et al, "Interpreting treatment effects in randomized trials," *BMJ*, 1998; 316.

Guyatt, G.H., MD et al., "Postscript," *Controlled Clinical Trials*, 1991; 12; 266S-269S.

Guyatt, G.H., MD et al, Measuring disease-specific quality of life in clinical trials, *CMAJ*, 1986; 134:889.

Hallberg, Leif et al, "Menstrual Blood Loss—A Population Study," *Goran, Acta obst. Gynec. Scandinav*, 1966; 45:320.

Hays, J. et al, Effects of Estrogen plus Progestin on health Related Quality of Life: N. Engl. J. Med.., 2003, 348;1839-54.

Hays, R. D. et al, "The Rand 36-Item Health Survey 1.0," *Health Economics*, 1993; 2: 217-227.

Heavy Menstrual Bleeding, Clinical Guideline, Jan. 2007.

Higham, J.M. et al, "Risk-Benefit Assessment of Drugs Used for the Treatment of Menstrual Disorders," *Drug Safety*, 1991; 6(3): 183-191.

Hoylaerts, M., et al, "Studies on the Mechanism of the Antifibrinolytic Action of Tranexamic Acid," *Biochimica et Biophysica Actra*, 673 (1981) 75-85.

Hurskainen, R., et al, "Combined Laboratory and diary method for objective Assessment of menstrual Blood loss"; Acta, Obstet. Gynecol. Scand. 1998, 77; 201-204.

Hurskainen, R., et al, "Quality of life and cost-effectiveness of levonorgestrel-releasing intrauterine system versus hysterectomy for treatment of menorrhagia: a radomized trial," *The Lancet*, 2001, 357.

Hypromellose, Wikipedia definition, p. 1-3 http://en. Wilkipedia.orgf/wiki/Hypromellose, downloaded on Jan. 16, 2009.

Information Sheet A.D.A.M., Inc. 1997-2007 (Internet)"Tranexamic acid", submitted to the USPTO on May 6, 2010, 6 pp.

Information Sheet: Transamin Capsules, with Product Information: Transamin Tablets 500 mg dated Feb. 1998.

Information Sheet: Transamin Otlo Pharmaceuticals, cap, tbs, injection, submitted to the USPTO on May 6, 2010.

Informtion Sheet LExi-comp: Tranexamic Acid, Brand names, 5 pp. (2008).

International Search Report from PCT/US2004/023528 dated Jan. 7, 2005.

International Search Report from PCT/US2005/20558 dated Nov. 8, 2005.

International Search Report from PCT/US2005/20563 dated Nov. 10, 2005.

Investigative report dated Apr. 7, 2010 and prepared by Chief Investigator D.C. Sharma of ClueWise Services, Pvt. Ltd. (India) concerning information sought on Mefro Pharmaceuticals and Terrance Pharma (both of India), specifically in relation to a Trexamic Rx product (tranexamic acid).(Reference All).

Jaeschke, R., et al, "Ascertaining the Minimal Clinically Important Difference," *Controlled Clinical Trials*, 1989; 10:407-415.

Jaeschke, R., et al, "Interpreting Changes in Quality-of-Life Score in N of 1 Randomized Trials," *Controlled Clinical Trials*, 1991; 12:226S-233S.

Jenkinson, C. et al., "Measuring change over time: a comparison of results from a global single item of health status and the multidimensional SF-36 health status survey questionnaire in patients presenting with menorraghia," *Quality of Life Survey*, 1994; 3:317-321.

Jenkinson, C., et al "Making sense of ambiguity: evaluation of internal reliability and face validity of the SF 36 questionnaire in women presenting with menorrhagia," *Quality in Healthcare*, 1996; 5: 9-12.

Jones, G.,' et al, "Health-related quality of life measurement in women with common benign gynecologic conditions: A systematic review," AJOG Reviews, 2002; 187; 501-11.

Juniper, E., et al, "Determining a Minimal Important Change in a Disease-Specific Quality of Life Questionaire", J. Clin. Epidemlol. vol. 47, No. 1, 81-87, 1994.

Kadir, R.A. et al, "Quality of life during menstration in patients with inherited bleeding disorders," *Hemophilia*, 1998; 4: 836-841.

Kadir, R.A., et al, "Management of excessive menstrual bleeding in women with hemostatic disorders," *Fertility and Sterility*, 2005; 865(5), 1352-1359.

Kaller H., Enterale Resorption, Verteilung und Elimination von 4-Ainomethylcyclohexancarbonsaure (AMCHA) und a-Aminocapronsure (ACS) beim Menschen, *Naunyn-Schmiedeberts Arch. Pharmak. U. exp. Path.* 256, 160-168 (1967).

Kennedy, A., et al, "Effects of Decision Aids for Menorrhagia on Treatment Choices, Health Outcomes and Costs," *JAMA*, 2002; 288: 2701-2708.

Kirshner, B., et al, "A Methodological Framework for Assessing Health Indices," *J Chron Dis*, 1985; 38: No. 1, 27-36.

Kjerulff, K.H., et al. "Patient satisfaction with results of hysterectomy", Am. J. Obstet. Gynecol., 2000; 183: 1440-7.

Kouides, PA et al, "Multisite management study of menorrhagia with abnormal laboratory haemostasis: a prospective crossover study of intranasal desmopression and oral tranexamic acid," *Br J Haemotol*, 2009; 145(2): 212-220.

Kriplani et al, "Role of tranexamic acid in management of dysfunctional uterine bleeding in comparison with medroxyprogesterone acetate," Journal of Obstetrics and Cynaecology, vol. 26, No. 7 (2006), pp. 673-678.

Kuppermann, M., et al, "Effect of Hysterectomy vs. Medical Treatment on Health-Related Quality of Life and Sexual Functioning," *JAMA* 2004; Mar. 2004; 291: No. 12.

Lakhani, K. P. et al, "Uterine artery blood flow parameters in women with dysfunctional uterine bleeding and uterine fibroids: the effects of tranexamic acid," *Ultrasound Obstet Gynecol* (1998); 11: 283-285.

Lamping D.L., et al., "Development and Validation of an Audit Instrument: the Prostate Outcomes Questionnaire", Br. J. Urology, 1998, 82, 49-62.

Lamping, D.L. et al, "Development and validation of the menorrhagia outcomes questionnaires," *British Journal of Obstetrics and Gynaecology*, 1998; 105: 766-779.

Lee et al., "Treatment of Menorrhagia with Tranxamic Acid," Fertility and Sterility, Oct. 18, 1997, suppl. 1, p. 96.

Lee, J. et al., "Treatment of Menorrhagia with Tranexamic Acid," *J. Soc. Obstet. Gynaecol. Can.*, 2000:22(109):794-8.

Lee et al., Controlled-Release Drug-Delivery Systems, Chapter 47 in Gennaro et al., Remington: The Science and Practice of Pharmacy, 20th Edition, Lippincott, Williams and Wilkins, pp. 903-929 (2000).

Leidy, N.K. et al., "Recommendations for Evaluation the Validity of Quality of Life Claims for Labeling and Promotion", ISPOR, Value in health, 1999; 2(2), 113-127.

Lethaby A, Farquhar C, Cooke I. Antifibrinolytics for heavy menstrual bleeding. *Cochrane Database of Systematic Reviews* 2000, Issue4;. The Cochrane Library, 2008 Issue 2.

Lethaby, A. et al, "Antifibrinolytics for heavy menstrual bleeding (Review)," *The Cochrane Collaboration*, 2008; issue 24.

Lethaby, A., et al, "Antifibrinolytics for heavy menstrual bleeding, (Review)" *The Cochrane Collaboration*, 2002; Issue 4.

Liu, Z., et al., "A Systematic Review Evaluation health-Related Quality of Life, Work Impairment, and Health-Care Costs and Utilization in Abnormal Uterine Bleeding" ISPOR, Value in health, 2007; 10(3), 183-194.

Lockhart, I., Comments on MHRA Consultation Arm 39; Request to Reclassify CYKIO-F 500 Mg. Tablets (Tranexamic Acid) from Prescription only Medicine (POM) to Pharmacy available (P); royal College of Physicians of Edinburgh., Feb. 27, 2007.

Longstaff, C., "Studies on the mechanisms of action of aprotinin and tranexamic acid as plasmin inhibitors and antifibrinolytic agents," *Blood Coagulation and Fibrinolysis*, vol. 5, 1994, pp. 537-542.

Lohr, K., et al., evaluating Quality of Life and Health Status Instruments: Development of Scientific Review Criteria, Clin. Therapeutics, vol. 18, No. 5, 1996, 979.

Lydick E., et al., "Interpretation of quality of life changes", Quality of life Research, 1993; 2, 221-226.

Mannucci, P.M., "Hemostatic Drugs", New England J. Medicine, vol. 339(4); 245-253. (1998).

Marjorbanks, J. et al, "Surgery versus medical therapy for heavy menstrual bleeding (Review)", The Cochrane Library, 2009, Issue 2.
Martindale—revision Nov. 28, 2001, Monograph, tranexamic acid (1726j).
McHorney, C.A. et al, "The MOS 36-Item Short-Form Health Survey (SF36) II, Psychometric and Clinical Test of Validity in Measuring Physical and Mental Health Constructs", Med. Care, 1993; 31(3): 247-263.
McHorney, C.A. et al, "The MOS 36-Item Short-Form Health Survey (SF36) III. Psychometric and Clinical Test of Data Quality, Scaling Assumptions, and Reliability Across Diverse Patent Groups", Med. Care, 1994; 32(1): 40-66.
Mehta, B.C. et al, "Epsilon-Amino-Caproic Acid in the Treatment of Menorrhagia," *Journal of Postgraduate Medicine*, 1977; 23(3): 121-123.
Melander, B., et al., "Biochemistry and Toxicology of Amikapron®; The Antifibrinolytically Active Isomer of (AMCHA.) (A Comparative Study with Aminocaproic Acid)," *Acta Pharmacol. Et Toxicol.* 1965, 22, 340-352.
Milsom, I. et al. "A comparison of flurbiprofen, tranexamic acid, and a levonorgestrel-releasing intrauterine contraceptive device in the treatment of idiopathic menorrhagia," *Am J Obstet Gynecol*, 1991; 194: 879-883.
Mohri, H., "High Dose of Tranexamic Acid for Treatment of Severe Menorrhagia in patients with von Willebrand Disease," *Journal of Thrombosis and Thrombolysis*, 14(3), 255-257, 2002.
Monograph Health Canada; Cyklokapron; solution: for IV Use, date May 2005.
Monograph: British Nat. Formulatory No. 43, 2002 sec. 2. 11 Antifibrolytic drugs and haemostatis; Tranexamic acid No. 123.
Moos, K., MDQ Form C, published by Western Psychological Services, 1989.
National Center for Women's and Children's Health: Heavy Menstrual Bleeding Full Guideline Draft, (Jul. 2006).
New Zealand Working Party Guidelines, "An evidence-based guideline for the management of heavy menstrual bleeding", N Z Medical Journal, 1999, 112; 174-7.
NICE Clinical Guideline 44, "Heavy Menstrual bleeding", Jan. 2007.
Nilsson, L., et al., "Treatment of Menorrhagia with an Antifibrinolytic Agent, Tranexamic Acid (AMCA)," *Acta obst. Et gynec. Scandinav.* 46, 572, 1967.
Nilsson, I., "Clinical pharmacology of aminocaproic and tranexamic acids," *J Clin Pathod*, 33, Suppl (Roy Coll Path), 14, 41-47. (1980).
Nilsson, L and Rybo, G, "Treatmetn of Menorrhagia with an Antifibrinolytic Agent, Tranexamic Acid (AMCA)," *Acta obst. Et gynec. Scandinav.*, 46, 572, 1967.
Ogston. D, "Current Status of Antifibrinolytic Drugs," *Blood Reviews*, 1989; (3): 1-4.
Ong. Y.L. et al, "Menorrhagia in von Willebrand disease successfully treated with single daily dose tranexamic acid," *Haemophilia*, 1998,4: 63-65.
Osoba, D., et al, "Evaluating Health-Related Quality of Life in Cancer Clinical Trial: The National Cancer Institute of Canada Clinical Trials Group Experience," *Value in Health*, 2007; 10: suppl 2, 1098-3015/07/S138.
Package Leaflet: Information for the User, Cycklo-f-500 mg film-coated tablet, Tranexamic acid (2007), 3 pp.
Package Leaflet: Information for the user, Cyklonova 500 mg film-coated tablet. Leaflet approved Dec. 12, 2005. pp. 1-3.
Park, Serena and Farquhar, CM, "A survey of practice preferences and attitudes of the New Zealand Guidelines for the management of heavy menstrual bleeding", Aust NZ J Obstet. Gynaecol 2002; 42, 4:376, p. 377-80.
Patent Abstracts of Japan Publicatin No. JP 07206660, *External Preparation for Skin*, Published Aug. 8, 1995.
Patent Abstracts of Japan Publication 1997 No. JP 09124878, *Gel Composition*, Published May 13, 1997.
Patent Abstracts of Japan Publication No. JP 06219942, *Gelatin Capsule Preparation Mixed With Tranexamic Acid*, Published Aug. 9, 1994.
Patent Abstracts of Japan Publication No. JP 0925542, Composition for Oral Cavity Application Published Sep. 30, 1997.
Patent Abstracts of Japan Publication No. JP 57059847, 4-Aminomethylcyclohexanecarboxylic Acid Derivative, published Apr. 10, 1982.
Patrick, D.L. et al, "Quality of Life of Women with Urinary Incontinence, Further development of the incontinence quality of Life Instrument (I-QOL)", Urology, 53: 71-76, 1999.
Patrick, D.L., et al, "Assessing the Clinical Significance of health related quality of life (HrQOL) improvements in anaemic cancer patients receiving epotin-alfa", European of Cancer, 39 (2003) 335-345.
Patrick, D.L., et al, "Patient-Reported Outcomes to Support Medical Product Labeling Claims: FDA Perspective," Patrick, D.L., et al, "Patient-Reported Outcomes to Support Medical Product Labeling Claims: FDA Perspective," *Value in Health*, 2007; 10: suppl 2, 1098-3015/07/S 125.
Pawar, A. et al., "Perceptions about quality of life in a school-based population of adolescents with menorrhagia: implications for adolescents with bleeding disorders", Haemophilia, 2008, 14, 579-583.
Peterson et al., Treatment of Menorrhagia with Tranexamic Acid, Acta Obstetrica et Gynecologica Scandinavica, 1983, Supp. 116, p. 70, 115.
Phillip, C.S., et al, "Development of a screening tool for identifying women with menorrhagia for haemostatic evaluation," *American Journal of Obstetrics and Gynecology*, 2008; 1998: Issue 2, 163.
Phillipp, C. S. et al., "Age and the Prevalence of Bleeding Disorders in women with Menorrhagia", Obstst Gynecol 2005; 105: 61-6.
Pilbrant, A., et al, "Pharmacokinetcis and Bioavailability of Tranexamic Acid," *Eur J Clin Pharmacol*, (1981) 20: 65-72.
Popo, V., MHRA, Consultant Doc.: ARM 39, Request to Reclassify a product from POM to P; Cyklo-F, Feb. 7, 2007.
Prentice, C.R.M., "Indications for Antifibrinolytic Therapy," *Thrombos. Diathes. Haemorrh.* (*Stuttg.*), 1975; 34: 634.
Preston J. T., et al, "Comparative study of tranexamic acid and norethisterone in the treatment of ovulatory menorrhagia, "*British Journal of Obstetrics and Gynaecology*, May 1995, vol. 102, pp. 401-406.
Price list detailing the prices of numerous Mefro Pharmaceutical (P) Ltd Products, including Tab, Trexamic and Tab trexamic-M (Reference A13), submitted to USPTO on Jul. 6, 2010.
Product catalog of Mefro Pharmaceuticals (P) Ltd. that lists Tab Trexamic and Tab Trexamic-M as available products (Reference A12), submitted to USPTO on Jul. 6, 2010.
Product Information Cyklokapron Pharmacia; South Africa; 500 mg tablets, 500 mg IV, 1g effervescent tablets; package insert dated Dec. 1999.
Product Information Cyklokapron® Pfizer Australia, most recent Amendment Mar. 11, 2008, pp. 1-8.
Product Information Kalnex Capsules (250mg), tablets (500 mg,) Injection, 1991.
Product Information, Cycklokapron, Tranexamic acid (CAS 1197-18-8), 26 pp., (2008).
Product Information: Amchafibrin, 500 mg, submitted to USPTO on May 6, 2010.
Product Information: Cyklokapon "Media, Pfizer," Injection, 500 mg tablets, dated Oct. 24, 2006.
Product Information: Cyklokapron Injectin, Ampoules 500 mg per 5ml, Pharmacia Limited UK, authorization date Feb. 9, 1987.
Product Information: Cyklokapron Pharmacia; US, 500 mg tablets and injection; package insert dated Oct. 2000.
Product Information: Cyklokapron tablets and injection; 100 mg/1ml water, Pharmacia & Upjohn revision Jun. 2008.
Product Information: Cyklonova 500 mg film coated tablets; product information date Oct. 5, 2007.
Product Information: Dalichi Pharmaceutical Co. Ltd., Transamin Injection and Transamin S injection; 250 mg/5 ml, 250 mg/2.5 ml and 1g/10ml. 14 pp. (1998).
Product Information: Dexa Medica, Traexid injection, 5% and injection 10% 9 pg. (2008).
Product Information: Proklot film coated tablet, 500 mg, submitted to USPTO on May 6, 2010.
Product Information: Teva Pharmaceutial Industries Ltd., HEXAPRON; 500 mg/5ml, 3 pg. (2003).

Product Information, Tranexamic Acid, downloaded from http://csi.micromedex.com/DKS/DATA/MT/MTMI/1726-j.HTM?Top=Yes (1 of 9) Nov. 4, 2003 10:05:51 AM.
Product Information: Tranexid, 250 mg capsules, 500 mg membrane coated tablets http://www.dexamedica, com/printview.php?cid+3&id=62, Sep. 11, 2008, 6 pp.
Product Information: Tranfib, tablets and injection, submitted to USPTO on May 6, 2010.
Product Information: Transamin Capsules, 250 mg tablets, 500 mg tablets, 50% powder, product information revision Jun. 2005.
Product Information: Transamin Capsules, dated Feb. 1998.
Product Information: Trexamic Rx (Tranexamic acid tablets BP 500 mg), marketed by Metfro Pharmaceuticals, Ltd, manufactured by Terrance Pharmaceuticals, Ltd,, p. 1, submitted to USPTO on May 6, 2010.
Product Information: Cyklokapron—tranexamic acid injection solution, 100 mg/1 ml. Pharmacia & Upjohn revision Jun. 2008.
Product Information: Cyklokapron KabiVitrumAB; US, 500 mg tablets and injection; package insert dated Jan. 1987.
Product Information: Cyklokapron tablets (PfizerAu, approval 2001) with PI version pfpcyk110308; PI Medsafe data sheet New Zealand 2008 (film coated tablet); and Pfizer data sheet (Spanish).
Product Information: Hemostan 250, 500 mg capsules, injection, submitted to USPTO on May 6, 2010.
Product Information: Tranon 500 mg film coated tablet, product information approved Apr. 16, 2008.
Product Monograph: Cyklokapron: Pfiezer Canada Control No. 086534; Tranexamic acid tablets BP and Tranexamic acid injection BP date: Sep. 10, 2003, control No. 086534.
Production Information: Cyklo-f 500 mg film coated tablet, authorization Jan. 31, 1997.
Production Information: Cyklokapron—tranexamic acid injection solutions, 100 mg/1ml. Pharmacia & Upjohn revision Jul. 2005, product registration, Jul. 31, 1968 (Dutch Language).
Production Information: Cyklokapron Tablets 500 mg. product authorization Feb. 2005.
Production Information: Cyklokapron Tablets 500 mg. film coat, product Jul. 31, 1968 with product information: cyklokapron 100 mg effervescent tablets, product authorization Dec. 7, 1995.
Protheroe, J., et al "The role of primary care in the diagnosis and management of menorrhagia: a qualitative study of women with menorrhagia," Primary Health Care Research and Development 2005: 6: 21-22.
Pulgdellivol, E. et al, "Pharmacokinetics and absolute bioavailability of intramuscular tranexamic acid in man," *International Journal of Clinical Pharmacology, Therapy and Toxicology*, 1985; 23; No. 6, 298-301.
Quantification of Menstrual Blood Loss, Review, The Obstetrician & Gynecologist, 2004; 6: p. 88-92.
Quixil solutions for sealant, date of first authorization Sep. 1999.
Radloff, L.S., "The CES-D Scale: A Self-Reported Depression Scale for Research in the General Population", App. Psychological. Measurement, 1977; 1(3), 385-401.
Ragab, M.I. et al, The Use of Tranexamic Acid (AMCA) in IUDs as an Anti-bleeding agent, Int. J. Gynacol Obstet, 1976; 14:137-141.
RANZCOG, NHC Guidelines, Mar. 1999.
Reid, P.C., et al., "Assessment of Menstrual Blood Loss using a Pictorial Chart: a Validation Study "British L. Obstetrics and Gynaecology, Mar. 2000, vol. 107, pp. 320-322.
Revicki, D.A., et al, "Interpreting and Reporting Results Based on Patient-Reported Outcomes," *Value in Health* 2007; 10: suppl 2, 1098-3015/07/S138.
Richter, H.E., et al., "Medroxyprogasterons acetate treatment of abnormal uterine bleeding: Factors predicting satisfaction", Am. J. Obstet. Gynecol, Jul. 2003, pp. 37-42.
Rothman, M.L. et al., "Patient Reported Outcomes: Conceputal Issues", Value in Health, vol. 10 Supp. 2, 2007, pp. S66-S75.
Ruta, D.A. et al, "Patient centered assessment of quality of life for patients with four common conditions," *Quality in Health Care*, 1999; 22-29.
Ruta, D.A. et al, Assessment of patients with Menorrhagia: how valid is a structured clinical history as a measure of health status, *Quality of Life Research*, 1995; 4: 33-40.

Ruta, D.A. et al, SF 36 health survey questionnaire: 1. Reliability in two patient based studies, *Quality in Health Care*, 1994; 3: 180-185.
Rybo G., "Plasminogen Activators n the Endometrium, I. Methodological Apects," *Acta obst. Et gynec. Scandinav.* 45, 411, 1966.
Rybo, "Tranexamic acid therapy—effective treatment in heavy menstrual bleeding." *Therapeutic Advances*, 1991; issue 4.
Santer, M. et al., "what aspects of periods are most bothersome for women reporting heavy menstrual bleeding? Community survey and qualitative study", BMC Women's Health 2007, 7:8.
Scientific Conclusions and Grounds for Amendment of the Summary of Product Characteristics Presented by the EMEA, Annex 1, p. 1-15, submitted to USPTO on May 6, 2010.
Scientific Advisory Committee, "Assessing health status and quality of life instruments; Attributes and review criteria", Quality of Life Research 11: 193-205, 2002.
Sculpher, M.J., et al., "Randomized trial comparing hysterectomy and transcervical endometrial resection: effect on health related quality of life and costs two years after surgery", Br. J, of Obstet. Gynaecol., 1996, 103,142-149.
Shankar, M. et al, "Review of quality of life: Menorrhagia in women with or without inherited bleeding disorder," *Haemophilia*, 2008; 14: 15-20.
Shapley, M., et al. "An epidemiological survey of symptoms of menstrual loss in the community", British Journal of General Practice, 2004, 54; 359-363.
Shapley, M., et al. "Why women consult with increased vaginal bleeding: a case-control study", British Journal of General Practice, 2002, 52, 108-113.
Shaw, R. W. et al, "Perceptiosn of women on the Impact of menorrhagia on their health using multi-attribute utility assessment," *British Journal of Obstetrics and Gynaecology*, Nov. 1998; 105: 1155-1159.
Shaw, R.W., "Assessment of medical treatments for Menorrhagia," *British Journal of Obstetrics and Gynaecology* 1994; vol. 101, suppl. 11:15-18.
Shin-Yakuzaigaku Souron (New General Pharmaceutics), Nankodo, revised edition vol. 3, Apr. 10, 1987, pp. 287-291 (Note: An English translation of Table 10.2 is included), 6 pp.
Siddiquil, Shahnaz Hasan, "Spectrum of Dysfunctional Uterine Bleeding and its Conservative Management", JCPSP 2003, vol. 13 (7):375-377.
Siegel, J.E. and Kouldes, P.A. Menorrhagia from a haematologist's point of view. Part II: Management Haemophilla (2002), 8, p. 339-347.
Silverman, E., "Your Drug Target Audience", The Scientist, Oct. 2007; 65-70.
Sindet-Pedersen, "Distribution of tranexamic acid to plasma and saliva after oral administration and mouth rinsing: a pharmacokinetic study," J. Clin. Pharmacol. 1987; 27; 1005.
Sloan, J.A., et al, "The Mayo Clinic manuscript Series Relative to the Discussion Dissemination, and Operationalization of the Food and Drug Administration Guidance on Patient Reported Outcomes", ISPOR, Values in health, 2007, 10 Supp2., S69-S63.
Sloan, J.A., et al. "Analysis and Interpretation of Results Based on Patient Reported Outcomes", ISPOR, Values in Health, 2007, 10, Supp2., S106-S115.
Smith, N.D., "Quality of Life Studies From the Perspective of an FDA Reviewing Statistician", Drug Inf. J. 1993, 27,617-623.
Stavchansky and McGinity, "Bioavailability in Tablet Technology", Ch. 6, in Lieberman et al., Pharmaceutical Dosage Form, $2^{th}$ Ed., vol. 2, Marcel Dekker, pp. 349-569 (1990).
Snyder, C.F., et al., "patient Reported Outcome Instrument Selection: Designing a Measuring Strategy" ISPOR, Values in Health, 2007, 10 Supp2., S76-S85.
Spies, J.B., et al., "The Fibroid Registry; Symptom and Quality of Life Status 1 year AfterTherapy", Obstet Gynecol 2005, 106; 1309-18.
Spies, J.B., et al., "The UFS-QOL, a New Disease-Specific Symptom and Health-Related Quality of Life Questionnaire for Leiomyomata", Obstet Gynecol 2002, 99; 290-300.
Srinil, S., et al., "Treatment of Idiopathic Menorrhagia with Tranexamic Acid", J Med Assoc. Thai 2005; 88(Suppl.2); S1-6.

Srinil, Sukanya, MD, "Treatment of Idiopathic Menorrhagia the Tranexamic Acid," *J. Med Assoc Thai*, 2005; 88: suppl 2.

Stanford School of Medicine, Div. Imm. & Rheu., "The Health Assessment Questionnaire", Jan. 19, 2001.

Stirk, J., et al., "Sensitivity and Specificity of Observer and Self-Report Questionnaires in major and minor Depression Following Myocardial Infarction" Psychosomatics, 2001: 42: 423-428.

Stirrat, Gordon M., "Choice of treatment for menorrhagia," The Lancet, Jun. 26, 1999, vol. 353, pp. 2175-2176.

Svahn C M, et al, "Absorption of Tranexamic Acid as a Prodrug in Healthy Volunteers," *Arznelm-Forsch/Drug* 38(1), Nr. 5 (1988).

Svahn, C. M. et al, "Tranexamic Acid Derivatives with Enhanced Absorption", Journal of Medicinal Chemistry, 1986, vol. 29, No. 4. p. 448-453.

Tapanainen, Juha S., "Medical Management of Menstrual Disorders", J.S. Tapanainen/International Congress Series 1266 (2004) 63-68.

Testa, M.A., et al., "Methods for Quality of Life Studies", Annu. Rev. Public Health, 1994, 15:535-59.

Thorsen S., "Differences in the Binding to Fibrin of Native Plasminogen and Plasminogen Modified by Proteolytic Degradation Influence of w-Aminocarboxylic Acids," Biochimica et Biophysica Acta, 393 (1975) 55-65—Elsevier Scientific Publishing Company, Amersterdam.

Tranexamic acid Product Description, p. T151-154 (1985).

Transamin Capsules (250mg), Tranexamic Acid Preparation, Product Description 2 pp. (2005).

Transamin, Transamin cap approved prescribing info, MMS Malaysia, downloaded Mar. 8, 2010 http://www.mims.com/Page__.aspx?menuid=Transamin+cap&CTRY=MY&brief., p. 1-6.

Transmin Tablets 500 mg, Tranexamic Acid Preparation, Product Description p. 1-2, (1991).

Treatment and Management of Women with Bleeding Disorders, clinical trials.gov (2005), downloaded from http://clinicaltrials.gov/?ct2/show/NCT00111215?cond=%22von+Willebrand+Disease%22 on Mar. 6, 2008, 5 pp.

Tsementzis, S.A, et al., "Fibrinolytic Activity After Subarachnoid Haemorrage and the Effects of Tranexamic Acid," *Acta Neurochir (Wien)*, vol. 103 (1990), pp. 116-121.

Turner, R. R., "Patient-Reported Outcomes: Instrument Development and Selection Issues," ISPOR, *Value in Health*, 2007; 10: sup. 2, S86-S93.

Van Den Akker, O., et al, "Pyscho physiological Responses in Women Reporting Severe Premenstrual Symptoms" Psychosomatic Medicine 51: 319-328 (1989).

van Eijkeran, M.A. et al, "Menorrhagia. Current Drug Treatment Concepts," *Drugs*. 1992; 43 (2) 201-209.

Varner, R. et al., "Medicine or Surgery (MS); a randomized clinical trial comparing hysterectomy and medical treatment in premenopausal women with abnormal bleeding", Controlled Clinical Trials, 25 (2004) 104-118.

Vemylen J., et al, "A Double blind study of the effect of tranexamic acid in essential menorrhagia." *Throm DiathHaemorrh.*, Dec. 31, 1968; 20(3): 583-587.

Verstraete, M., "Clinical Application of Inhibitors if Fibrinolysis," *Drugs*, 29: 236-261 (1985).

Vilos, GA, et al, "Guidelines for the management of abnormal uterine bleeding" J. Obstet. Gynaecol Can., 2001; 23; 704-709.

Wallenstien, G., et al, "Development and Validation of the Premenstrual Symptoms Impact Survey (PMSIS): A disease-specific Quality of Life Assessment Tool," *Journal of Women's Health*, 2008; 17: No. 3.

Waltzman et al, "Effects of Tranexamic Acid on the Coagulation and Fibrinolytic Systems in Pregnancy Complicated by Placental Bleeding," New Toxicology for Old Arch. Toxicol., Suppl. 5 (1982), pp. 214-220.

Ware, J.E., Jr. et al, "The MOS 36-Item Short-Form Health Survey (SF36)," *Med. Care*, 1992; 30: 473-483.

Warner, P.E. et al, "Menorrhagia I: Measured blood loss, clinical feathers, and outcome in women with heavy periods: A survey with follow-up data," *Am. J. Obstetrics and Gynecology*, 2004: 190: 1216-23.

Warner, P.E., et al, "Menorrhagia II: Is the 80mL blood loss criterion useful in management of complaint of menorrhagia?" *Am. J. Obstetrics and Gynecology*, 2004; 190: 1224-29.

Wellington et al Tranexamic Acid, A Review of its Use in the Management of Menorrhagia Drugs, 63(13), p. 1417-1433, 2003.

Westrom, Lars, MD et al, "Effect of Tranexamic Acid (ACMCA) in Menorrhagia with Intrauterine Contraceptive Devices," *J. of Reproductive Medicine*, 1970; 5: No. 4.

Wiegel, M., et al., "The Female Sexual Function Index (FSFI): Cross Validation and Development of Clinical Cutoff Scores", J Sex Martial Ther. 2005, 31; 1-20.

Wilson, I, B., et al., "Linking Clinical Variables with Health Related Quality of Life: A conceptual model of Patient Outcomes", JAMA 1995, 273(1), 59-65.

Wilson et al., "Physiological Pharmaceutics Biological Barriers to Drug Absorption", Horwod Ellis, Chichester, Chapter 4, pp. 47-70 (1989).

Winkler, U.H., "the effect of tranexamic acid on the quality of life of women with heavy menstrual bleeding," *European J. Obstetrics & Gynecology and Reproductive Biology*, 2001; 99: 238-243.

Working Party for Guidelines for the Management of Heavy Menstrual Bleeding. "An evidence-based guideline for the management of heavy menstrual bleeding," NZ Med J; 1999; 112: 174-7.

Wyrwich, K.W. et al., "Further Evidence Supporting an SEM-Based Criterion for Identifying Meaningful Intra-Individual Changes in health Related quality of Life", J. Clin. Epidemiol. 2; 861-873. vol. 52, (1999).

Wyrwich, K.W. et al., "Identifying meaningful intra-individual change standards for health related quality of life measures", J. Evaluation in Clinical Practice, 2000, 6, 1, 39-49.

Wyrwich, K.W. et al., "Linking Clinical relevance and Statistical Significance in Evaluating Intra-Individual Changes in health Related quality of Life", Med. Care 1999 37 (5), 469-478.

Yikorkala, O., et al, "Comparison between antifibrinolytic and antiprostaglandin treatment in the reduction of increased menstrual blood loss in women with intrauterine contraceptive devices," *British Journal of Obstetrics and Gynaecology*, 1983; 80: 87-83.

Zee, B.C., "Growth Curve model Analysis for Quality of Life Data", Statist. Med., 17, 757-766 (1998).

Advisory Action dated Oct. 23, 2007 for U.S. Appl. No. 10/631,371, 3 pp.

Advisory Action dated Jun. 13, 2011 for U.S. Appl. No. 11/346,710, 3 pp.

Advisory Action dated Dec. 12, 2011 for U.S. Appl. No. 12/228,489.

Applicant's Accelerated Examination Support Document filed Feb. 26, 2010, U.S. Appl. No. 12/714,181, 6 pp.

Applicant's Pre-examination Search Statement filed Feb. 26, 2010, U.S. Appl. No. 12/714,181, 6 pp.

Applicant's Response to Final Office Action dated Jun. 14, 2007, filed Oct. 4, 2007, U.S. Appl. No. 10/631,371.

Applicant's Response to non-final Office Action dated Dec. 15, 2006, filed Mar. 13, 2007, U.S. Appl. No. 10/631,371, 9 pp.

Attorney B. Jefferson Boggs et al., Watson Laboratories, Inc., Florida's Initial Disclosure of Non-Infringement, Invalidity and Unenforceability Contentions to Ferring B.V., pp. 1 and 7-15, dated Jan. 5, 2012.

Attorney B. Neighbarger et al., First Amended Answer, Affirmative Defenses and Counter-claims to Complaint for Patent Infringement, Case No. 11-cv-00481-RCJ-VPC, D. Nev., 8 pp., dated Feb. 28, 2012.

Attorney B. Neighbarger et al., Second Amended Answer, Affirmative Defenses and Counter-claims to Complaint for Patent Infringement, Case No. 11-cv-00481-RCJ-VPC, D. Nev., 9 pp., dated Mar. 12, 2012.

Attorney Kevin W. McCabe, Notice Letter Regarding Paragraph IV Certification Against U.S. Patent No. 7947739 to Tranexamic Acid Formulations Pursuant to Section 505(j)(2)(B)(ii) of the Federal Food, Drug, and Cosmetic Act, dated May 27, 2011 (11 pages).

Attorney Kevin W. McCabe, Notice Letter Regarding Paragraph IV Certification Against U.S. Patent No. 8022106 to Tranexamic Acid Formulations Pursuant to Section 505(j)(2)(B)(ii) of the Federal Food, Drug, and Cosmetic Act, dated Oct. 12, 2011 (10 pages).

Attorney M. Rounds et al., First Amended Answer, Affirmative Defenses and Counter-claims to Complaint for Patent Infringement, Case No. 11-cv-004810RCJ-VPC, D. Nev., 16 pp., dated Feb. 28, 2012.

Attorney Michael D. Rounds et al., Watson's Points and Authorities in Opposition to Ferring's Motion to Dismiss Watons's Amended Second Counterclaims for Invalidty, Case No. 11-cv-00481-RCJ-VPC, D. Nev., 123 pp., dated Apr. 2, 2012.

Decision by USPTO dated Mar. 31, 2010 for Petition to Make Special, U.S. Appl. No. 12/714,181, 4 pp.

*Ferring B.V. v. Watson Labs., Inc.*, Order by Robert C. Jones, U.S. District Judge, District of Nevada, dated Feb. 6, 2013, 19 pp.

Final Rejection dated Oct. 12, 2010 for Japanese Appl. No. 2006-521917 (with English translation), 6 pp.

Interview Summary issued dated Apr. 19, 2011 for U.S. Appl. No. 11/346,710, 3 pp.

Janet Vaughn, Director, Regulatory Affairs, Watson Laboratories Florida, Notification of Certification of Invalidity and/or Noninfringement for U.S. Patent No. 8,022,106 Pursuant to Section 505(j)(2)(B)(iv) of the Federal Food, Drug and Cosmetic Act, dated Oct. 12, 2011 (15 pages).

Janet Vaughn, Director, Regulatory Affairs, Watson Laboratories Florida, Notification of Certification of Invalidity and/or Noninfringement of U.S. Patent No. 7947739 Pursuant to Section 505(j)(2)(B)(iv) of the Federal Food, Drug, and Cosmetic Act, dated May 24, 2011 (16 pages).

Janet Vaughn, Director, Regulatory Affairs, Watson Laboratories Florida, Notification of Invalidity and/or Noninfringement for U.S. Patent No. 8,273,795 Pursuant to §505(j)(2)(B)(iv) of the Federal Food, Drug, and Cosmetic Act, dated Nov. 5, 2012, 11 pp.

Notice of Allowance dated Apr. 8, 2011, U.S. Appl. No. 12/714,181, 9 pg.

Notice of Panel Decision from Pre-Appeal Brief Review dated Feb, 7, 2013 for U.S. Appl. No. 12/433,247.

Notice of Rejection dated Aug. 17, 2010 for Japanese Appl. No. 2007-523556 (with English translation), 11 pg.

Notice of Rejection dated Aug. 2, 2011, Japanese Appl. No. 2006-521917, 3 pg.

Notice of Rejection dated Aug. 2, 2011, Japanese Appl. No. 2011-028472, 7 pg.

Notice of Rejection dated Dec. 20, 2011, Japanese Appl. No. 2007-523555, 3 pg.

Notice of Rejection dated Oct. 25, 2011, Japanese Appl. No. 2007-523556, 2 pg.

Notice of Rejection dated Sep. 29, 2009 for Japanese Appl. No. 2006-521917 (with English translation), 25 pg.

Notice of Rejection dated Sep. 3, 2010 for Japanese Appl. No. 2007-523555 (with English translation), 11 pg.

Notice of Rejection dated Jan. 29, 2013 for Japanese Appl. No. 2011-062281, 5 pgs.

Office Action (Examiner Interview Summary Record) dated Oct. 28, 2008 for U.S. Appl. No. 10/631,371, 2 pg.

Office Action (Final Rejection) dated Dec. 6, 2010 for U.S. Appl. No. 11/346,710, 12 pg.

Office Action (Final Rejection) dated Jun. 14, 2007 for U.S. Appl. No. 10/631,371, 9 pg.

Office Action (Final Rejection) dated Sep. 9, 2010 for U.S. Appl. No. 12/220,241, 8 pg.

Office Action (final) dated Jun. 28, 2012 for U.S. Appl. No. 12/433,247.

Office Action (final) dated Aug. 25, 2010, U.S. Appl. No. 12/714,181, 11 pg.

Office Action (Final) dated Aug. 9, 2011 for U.S. Appl. No. 12/228,489.

Office Action (Non-final) dated Oct. 25, 2011 for U.S. Appl. No. 12/433,247.

Office Action (Non-Final) dated Dec. 15, 2006 for U.S. Appl. No. 10/631,371, 6 pg.

Office Action (Non-Final) dated Mar. 13, 2008 for U.S. Appl. No. 10/631,371, 7 pg.

Office Action (Non-Final) dated Mar. 18, 2010 for U.S. Appl. No. 11/346,710, 9 pp.

Office Action (Non-Final) dated Feb. 5, 2010 for U.S. Appl. No. 12/220,241, 7 pg.

Office Action (Non-Final) dated Jan. 23, 2008 for U.S. Appl. No. 11/072,162, 6 pg.

Office Action (Non-Final) dated Jul. 30, 2010 for U.S. Appl. No. 12/433,408, 7 pg.

Office Action (non-final) dated Apr. 27, 2010, U.S. Appl. No. 12/714,181, 8 pg.

Office Action (non-final) dated Jul. 1, 2010, U.S. Appl. No. 12/714,181, 11 pg.

Office Action (Non-Final) dated Nov. 8, 2010 for U.S. Appl. No. 12/228,489, 16 pg.

Office Action (non-final) dated Dec. 3, 2010, U.S. Appl. No. 12/714,181, 17 pg.

Office Action (Non-Final) dated Oct. 25, 2011 for U.S. Appl. No. 12/433,247, 33 pg.

Office Action (Restriction Requirement) dated May 17, 2011 for U.S. Appl. No. 12/433,247.

Office Action (Restriction Requirement) dated Aug. 17, 2009 for U.S. Appl. No. 11/346,710, 7 pg.

Office Action (Restriction Requirement) dated Aug. 25, 2006 for U.S. Appl. No. 10/631,371, 6 pg.

Office Action (Restriction Requirement) dated Jul. 20, 2010 for U.S. Appl. No. 12/228,489, 5 pg.

Office Action (Restriction Requirement) dated Feb. 17, 2010 for U.S. Appl. No. 12/433,408, 8 pg.

Office Action (Restriction Requirement) dated Nov. 27, 2007 for U.S. Appl. No. 11/072,162, 9 pg.

Office Action (Restriction Requirement) dated Oct. 20, 2009 for U.S. Appl. No. 12/220,241, 9 pg.

Office Action (Restriction Requirement) dated Feb. 14, 2008 for U.S. Appl. No. 11/072,194, 7 pg.

Office Action (Restriction Requirement) dated Sep. 12, 2012 for U.S. Appl. No. 13/230,902.

Office Action (Restriction Requirement) dated Feb. 11, 2013 for U.S. Appl. No. 13/620,148.

Office Action (Restriction Requirement) dated Dec. 2, 2011 for U.S. Appl. No. 13/016,800.

Office Action dated Jun. 29, 2011 for U.S. Appl. No, 12/283,694, 27 pg.

Office Action dated Mar. 1, 2012 for U.S. Appl. No. 12/283,694, 18 pg.

Ross Maclean, VP Global Regulatory Affairs, Letter from Apotex Inc. to Ferring B.V., dated Nov. 5, 2012, 10 pg.

TRANEXAMIC ACID FORMULATIONS

CROSS-REFERENCE TO RELATED APPLICATIONS

This application is a continuation of U.S. patent application Ser. No. 12/228,489 filed on Aug. 13, 2008, which is pending which is a continuation of U.S. patent application Ser. No. 11/072,194 filed Mar. 4, 2005 which claims the benefit of U.S. Provisional Application No. 60/550,113, filed Mar. 4, 2004, and U.S. Provisional Application No. 60/592,885, filed Jul. 30, 2004. The disclosures of each of the prior applications is hereby incorporated by reference in its entirety.

FIELD OF THE INVENTION

The invention is directed to modified release oral tranexamic acid formulations that preferably minimize or eliminate undesirable side effects and methods of treatment with these formulations.

BACKGROUND OF THE INVENTION

Tranexamic acid (trans-4-(aminomethyl)cyclohexanecarboxylic acid, Cyklokapron® (Pfizer) is an antifibrinolytic agent. That is, it helps to prevent lysis or dissolution of a fibrin clot which forms in the normal physiologic process of hemostasis. Its mechanism of action is as a competitive inhibitor of plasminogen activation, and as a noncompetitive inhibitor of plasmin; both plasminogen and plasmin are activators of fibrinolysis and active clot-lysing agents. Tranexamic acid thus helps to stabilize fibrin clots, which in turn maintains coagulation and helps to control bleeding.

Tranexamic acid is used to control excess bleeding, for example, excess bleeding that occurs during dental procedures in hemophiliacs and for heavy bleeding during menstruation (menorrhagia). Women suffering from menorrhagia are typically treated orally with 500 mg tranexamic acid tablets administered three or four times daily with a total daily dose ranging from 3 grams/day (two tablets every eight hours) to 6 grams/day (three tablets every six hours). However, this treatment may cause adverse gastrointestinal reactions, including nausea, vomiting, diarrhea, and cramping, etc. These gastrointestinal side effects are due to the quantity of tranexamic acid and/or rapid rate of release of tranexamic acid into the stomach with each dose, as well as the large quantity of excipients used in the tablet formulation that are introduced into the stomach. Such side effects, in addition to the cramping, bloating, pain, and other symptoms that may accompany menses, are undesirable, and a formulation of tranexamic acid is needed which will reduce or eliminate these side effects.

SUMMARY OF THE INVENTION

Formulations of tranexamic acid which minimize or eliminate the undesirable gastrointestinal side effects in patients on oral tranexamic acid therapy, e.g. women treated for menorrhagia (heavy menstrual bleeding) are disclosed. The present invention is directed in part to a modified release formulation, formulated so that the release of tranexamic acid thereof from the dosage form occurs in a designed fashion to prevent a bolus of tranexamic acid being introduced into the stomach and available for dissolution in the gastric contents. Such modified release formulations reduce the concentration of tranexamic acid dissolved in the stomach contents such as e.g., preventing a large bolus of tranexamic acid being introduced in the stomach. The beneficial effect of this reduced tranexamic acid concentration is to lower the amount of tranexamic acid in the gastric contents so that there are fewer adverse effects with tranexamic acid therapy. This reduction in adverse effects preferably results in improved patient compliance with therapy, because preferably patients will not intentionally miss taking a dose to avoid these adverse side effects. Physicians will also preferably be more likely to initiate and maintain tranexamic acid treatment for their patients because of the reduced patient complaints.

It is an object of the invention to provide an oral dosage form comprising tranexamic acid which is suitable for administration on a two or three times a day basis to humans.

It is a further object of the invention to provide a modified release oral dosage form comprising tranexamic acid and a modified release material which provides for the modified release of the tranexamic acid and is suitable for administration on a two or three times a day basis.

It is a further object of certain embodiments of the present invention to provide a modified release oral dosage form comprising tranexamic acid and a modified release material which minimizes or eliminates the undesirable gastrointestinal side effects in patients on oral tranexamic acid therapy while maintaining or improving the therapeutic effect of tranexamic acid.

It is a further object of certain embodiments of the present invention to provide a method of treating a patient suffering from heavy menstrual bleeding (menorrhagia) by orally administering to the patient one or more dosage forms comprising tranexamic acid and a modified release material which provide(s) for therapeutically effective levels of tranexamic acid suitable for two or three times a day administration.

The above advantages and objects and others can be achieved by virtue of the present invention which is directed in part to a modified release oral dosage form comprising tranexamic acid or a pharmaceutically acceptable salt thereof and a modified release material which provides for the modified release of the tranexamic acid or pharmaceutically acceptable salt thereof from the dosage form such that the dosage form is suitable for administration on a two or three times a day basis; said dosage form providing an in-vitro dissolution release rate of the tranexamic acid or pharmaceutically acceptable salt thereof, when measured by a USP 27 Apparatus Type II Paddle Method @ 50 RPM in 900 ml water at 37±0.5° C., of less than about 70% by weight tranexamic acid or pharmaceutically acceptable salt thereof released at about 45 minutes and about 100% by weight of said tranexamic acid or pharmaceutically acceptable salt thereof released by about 120 minutes.

In certain embodiments, the present invention is directed to a method of treating a patient in need of tranexamic acid or pharmaceutically acceptable salt thereof therapy comprising administering to the patient about 1300 mg of tranexamic acid or pharmaceutically acceptable salt thereof in at least one oral dosage form comprising said tranexamic acid or pharmaceutically acceptable salt thereof and a modified release material which provides a mean maximum plasma concentration ($C_{max}$) of tranexamic acid of from about 5 to about 17.5 mcg/ml, preferably from about 6.5 to about 15 mcg/ml, more preferably from about 9 to about 14.5 mcg/ml after single dose oral administration to humans.

In certain embodiments, the invention is further directed to a method of treating a patient in need of tranexamic acid or pharmaceutically acceptable salt thereof therapy comprising administering to the patient about 1300 mg of tranexamic acid or pharmaceutically acceptable salt thereof in at least one oral dosage form comprising said tranexamic acid or pharmaceutically acceptable salt thereof and a modified release material which provides a mean maximum plasma concentration ($C_{max}$) of tranexamic acid of from about 5 to about 25 mcg/ml, preferably from about 10 to about 20 mcg/ml, more preferably from about 12.5 to about 17.5 mcg/ml, most preferably about 15 to about 17 mcg/ml after steady state oral administration to humans.

In certain embodiments, the modified release oral dosage form of the present invention provides a mean $T_{max}$ of tranexamic acid at from about 1 to about 5.5 hours, preferably at from about 2 to about 4 hours, more preferably at from about 2 to about 3.5 hours after oral administration of the dosage form to humans.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of less than about 40% by weight tranexamic acid or pharmaceutically acceptable salt thereof released at about 15 minutes, less than about 70% by weight tranexamic acid or pharmaceutically acceptable salt thereof released at about 45 minutes, and not less than 50% by weight tranexamic acid or pharmaceutically acceptable salt thereof released at about 90 minutes.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of about 0% to about 40% by weight tranexamic acid or pharmaceutically acceptable salt thereof released at about 15 minutes, from about 20% to about 60% by weight tranexamic acid or pharmaceutically acceptable salt thereof released at about 30 minutes, from about 40% to about 65% by weight tranexamic acid or pharmaceutically acceptable salt thereof released at about 45 minutes, from about 50% to about 90% by weight tranexamic acid or pharmaceutically acceptable salt thereof release at about 60 minutes, and not less than 60% by weight tranexamic acid or pharmaceutically acceptable salt thereof released at about 90 minutes.

In certain embodiments, the invention is further directed to a modified release oral dosage form comprising tranexamic acid or pharmaceutically acceptable salt thereof and a modified release material, which provides for a bioavailability of tranexamic acid of greater than 40%, from about 41% to about 60%, preferably from about 42% to about 50%, more preferably about 45% after oral administration to humans In certain embodiments, the present invention is further directed to a modified release oral dosage form comprising from about 585 to about 715 mg of tranexamic acid or pharmaceutically acceptable salt thereof, preferably about 650 mg of tranexamic acid or pharmaceutically acceptable salt thereof, and a modified release material which provides for the modified release of the tranexamic acid or pharmaceutically acceptable salt thereof from the dosage form such that the dosage form is suitable for administration on a two or three times a day basis.

In certain embodiments, the present invention is directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis, the dosage form providing a reduction of at least one side effect selected from the group consisting of headache, nausea, vomiting, diarrhea, constipation, cramping, bloating, and combinations thereof, as compared to an equivalent amount of tranexamic acid or pharmaceutically acceptable salt thereof in an immediate release oral dosage form when administered across a patient population.

In certain embodiments, the present invention is directed to a modified release oral dosage form comprising tranexamic acid or pharmaceutically acceptable salt thereof and a modified release excipient, said dosage form providing for the release of the tranexamic acid or pharmaceutically acceptable salt thereof which is slower than an immediate release oral dosage form and faster than a controlled release oral dosage form, such that the modified release oral dosage form is suitable for administration two or three times a day.

In certain embodiments, the invention is further directed to a modified release oral dosage form comprising about 650 mg of tranexamic acid or pharmaceutically acceptable salt thereof and a modified release material, the dosage form being suitable for oral administration on a three times a day basis, and the dosage form providing a mean maximum plasma concentration ($C_{max}$) of tranexamic acid of from about 5 to about 17.5 mcg/ml, preferably from about 6.5 to about 15 mcg/ml, more preferably from about 9 to about 14.5 mcg/ml per 1300 mg tranexamic acid after single dose oral administration to humans.

In certain embodiments, the invention is further directed to a modified release oral dosage form comprising about 650 mg of tranexamic acid or pharmaceutically acceptable salt thereof and a modified release material, the dosage form being suitable for oral administration on a twice a day basis, and the dosage form providing a mean maximum plasma concentration ($C_{max}$) of tranexamic acid of from about 5 to about 40 mcg/ml, preferably from about 10 to about 30 mcg/ml per 1950 mg tranexamic acid after single dose oral administration to humans.

In certain embodiments, the invention is further directed to a modified release oral dosage form comprising about 650 mg of tranexamic acid or pharmaceutically acceptable salt thereof and a modified release material, the dosage form being suitable for oral administration on a three times a day basis, and the dosage form providing a mean plasma concentration of tranexamic acid of from about 5 to about 25 mcg/ml, preferably from about 7.5 to about 15 mcg/ml, more preferably from about 8 to about 10 mcg/ml, most preferably about 9 mcg/ml per 1300 mg tranexamic acid after steady state oral administration to humans.

In certain embodiments, the invention is further directed to a modified release oral dosage form comprising about 650 mg of tranexamic acid or pharmaceutically acceptable salt thereof and a modified release material, the dosage form being suitable for administration on a three times a day basis, and the dosage form providing a mean maximum plasma concentration ($C_{max}$) of tranexamic acid of from about 5 to about 25 mcg/ml, preferably from about 10 to about 20 mcg/ml, more preferably from about 12.5 to about 17.5 mcg/ml, most preferably about 15 to about 17 mcg/ml per 1300 mg tranexamic acid after steady state oral administration to humans.

In certain embodiments, the invention is further directed to a modified release oral dosage form comprising about 650 mg of tranexamic acid or pharmaceutically acceptable salt thereof and an modified release material, the dosage form being suitable for administration on a three times a day basis, and the dosage form providing a mean plasma trough concentration of tranexamic acid or pharmaceutically acceptable salt thereof of from about 2 to about 10 mcg/ml, preferably from about 3 to about 7.5 mcg/ml, more preferably about 4 to about 7 mcg/ml, most preferably about 5 to about 6 mcg/ml per 1300 mg tranexamic acid or after steady state oral administration to humans.

In certain embodiments, the invention is further directed to a method of treating a patient with a therapeutically effective amount of tranexamic acid or pharmaceutically acceptable salt thereof comprising administering to the patient two dosage forms of the present invention, each dosage form comprising from about 585 mg to about 715 mg of tranexamic acid or pharmaceutically acceptable salt thereof, preferably about 650 mg tranexamic acid or pharmaceutically acceptable salt thereof, and a modified release material such that the dosage form is suitable for oral administration on a three times a day basis.

In certain embodiments, the invention is further directed to a method of treating a' patient with a therapeutically effective amount of tranexamic acid or pharmaceutically acceptable salt thereof comprising administering to the patient three dosage forms of the present invention, each dosage form comprising from about 585 mg to about 715 mg, preferably about 650 mg tranexamic acid or pharmaceutically acceptable salt thereof, and a modified release material such that the dosage form is suitable for oral administration on a twice a day basis.

In certain embodiments, the invention is directed to a dose of tranexamic acid or pharmaceutically acceptable salt thereof comprising two unit dosage forms of a modified release formulation, each unit dosage form of said modified release formulation comprising from about 585 mg to about 715 mg, preferably about 650 mg of tranexamic acid or pharmaceutically acceptable salt thereof, and a modified release material which provides for the release of the tranexamic acid or pharmaceutically acceptable salt thereof from the dosage form such that the dose provides a therapeutic effect when administered three times a day.

In certain embodiments, the invention is directed to a dose of tranexamic acid comprising three unit dosage forms of a modified release formulation, each unit dosage form of said modified release formulation comprising from about 585 mg to about 715 mg, preferably about 650 mg of tranexamic acid or pharmaceutically acceptable salt thereof, and a modified release material which provides for the release of the tranexamic acid or pharmaceutically acceptable salt thereof from the dosage form such that the dose provides a therapeutic effect when administered twice a day.

In certain preferred embodiments, the invention is further directed to a modified release oral dosage form including tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of about 0% to about 40% by weight tranexamic acid or pharmaceutically acceptable salt thereof released at about 15 minutes, from about 20% to about 60% by weight tranexamic acid or pharmaceutically acceptable salt thereof released at about 30 minutes, from about 40% to about 80% by weight tranexamic acid or pharmaceutically acceptable salt thereof released at about 45 minutes, from about 50% to about 95% by weight tranexamic acid or pharmaceutically acceptable salt thereof release at about 60 minutes, and not less than about 60% by weight tranexamic acid or pharmaceutically acceptable salt thereof released at about 90 minutes.

In certain preferred embodiments, the invention is further directed to a modified release oral dosage form including tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides a dissolution release rate in-vitro of the tranexamic acid or pharmaceutically acceptable salt thereof when measured by the USP 27 Apparatus Type II Paddle Method @ 50 RPM in 900 ml water at 37±0.5° C. of about 14% to about 22% by weight tranexamic acid or pharmaceutically acceptable salt thereof released at about 15 minutes, from about 32% to about 50% by weight tranexamic acid or pharmaceutically acceptable salt thereof released at about 30 minutes, from about 47% to about 71% by weight tranexamic acid or pharmaceutically acceptable salt thereof released at about 45 minutes, from about 61% to about 92% by weight tranexamic acid or pharmaceutically acceptable salt thereof release at about 60 minutes, and from about 79% to about 100% by weight tranexamic acid or pharmaceutically acceptable salt thereof released at about 90 minutes.

In certain embodiments, the invention is directed to a modified release oral dosage form comprising tranexamic acid or pharmaceutically acceptable salt thereof and an effective amount of a modified release excipient such that the dosage form releases from about 10% to about 25% by weight tranexamic acid or pharmaceutically acceptable salt thereof every 15 minutes when measured in vitro utilizing the USP 27 Apparatus Type II Paddle Method @ 50 RPM in 900 ml water at 37±0.5° C. In certain preferred embodiments, the dosage form releases about 18% to about 23% by weight tranexamic acid or pharmaceutically acceptable salt thereof every 15 minutes when measured in vitro utilizing the USP 27 Apparatus Type II Paddle Method @ 50 RPM in 900 ml water at 37±0.5° C. Most preferably, the dosage form releases about 100% of said tranexamic acid or pharmaceutically acceptable salt thereof within about 120 minutes when measured in vitro utilizing the USP 27 Apparatus Type II Paddle Method @ 50 RPM in 900 ml water at 37±0.5° C. In certain embodiments, the dosage form releases about 1% of said tranexamic acid or pharmaceutically acceptable salt thereof every minute when measured in vitro utilizing the USP 27 Apparatus Type II Paddle Method @ 50 RPM in 900 ml water at 37±0.5° C.

In certain preferred embodiments, the modified release oral dosage form of the invention further provides a mean transit time of said tranexamic acid of 7.70±0.72 hours when administered across a patient population.

In certain preferred embodiments, the modified release oral dosage form of the invention further provides a mean absorption time of said tranexamic acid of 4.18±0.70 hours when administered across a patient population.

In certain further embodiments, the modified release oral dosage form of the present invention provides confidence intervals derived from ln-transformed pharmacokinetic kinetic parameters $AUC_{0-t}$, $AUC_{inf}$ and $C_{max}$ for tranexamic acid in plasma which are within a 80-125% range of an immediate release formulation including an equivalent amount of tranexamic acid when administered across a patient population under fasted conditions.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides less than about 20 percent incidence of headache as a side effect after single dose oral administration across a patient population.

In certain embodiments, the invention is further directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis and the dosage form provides less than about 10 percent incidence of nausea as a side effect when administered across a patient population, less than about 7 percent incidence of nausea when administered across a patient population, preferable less than about 5 percent incidence of nausea as a side effect when administered across a patient population, more preferably less than about 2 percent incidence of nausea as a side effect after single dose oral administration across a patient population.

In certain embodiments, the modified release oral dosage form of the present invention provides less CNS side effects (e.g., headache), less GI side effects (e.g., nausea), or combination thereof in comparision to an equivalent amount of tranexamic acid or pharmaceutically acceptable salt thereof in an immediate release formulation when administered across a patient population. Additionally or alternatively, in certain embodiments the dosage form provides less CNS side effects (e.g., headache), less GI side effects (e.g., nausea), or combination thereof in comparision to a therapeutically equivalent amount of tranexamic acid administered intravenously in five minutes or less across a patient population.

In certain embodiments, the modified release oral dosage form of the present invention provides for the reduction of at least one side effect as compared to an immediate release oral dosage form including an equivalent amount of tranexamic acid or pharmaceutically acceptable salt thereof, when the immediate release dosage form is administered across a same or different population of patients as said modified release dosage form, and wherein said immediate release dosage form releases all of said tranexamic acid or pharmaceutically acceptable salt thereof within about 45 minutes when measured in vitro utilizing the USP 27 Apparatus Type II Paddle Method @ 50 RPM in 900 ml water at 37±0.5° C. Such side effects can be for example, headache, nausea, vomiting, diarrhea, constipation, cramping, bloating, and combinations thereof.

In certain embodiments, the modified release oral dosage form of the present invention provides a mean transit time of tranexamic acid which is at least about 20 minutes longer, preferably about 30 minutes longer, than an immediate release formulation including an equivalent amount of tranexamic acid when administered across a patient population.

In certain embodiments, the dosage form of the present invention provides a mean absorption time of tranexamic acid which is at least about 20 minutes longer, preferably about 30 minutes longer, than an immediate release formulation including an equivalent amount of tranexamic acid when administered across a patient population.

In certain preferred embodiments, the therapeutically effective dose of the tranexamic acid or pharmaceutically acceptable salt thereof is provided via the administration of two or more dosage units. For example, if the dosage unit comprises 650 mg of tranexamic acid or pharmaceutically acceptable salt thereof and the dose for administration is about 1300 mg then two dosage units would be administered to a patient in need of such treatment, or for example, when the dose for administration is 1950 mg, three dosage units would be administered.

In certain preferred embodiments, the invention is further directed to a method of treating a patient with one or more modified release oral dosage forms comprising tranexamic acid or pharmaceutically acceptable salt thereof and a modified release material, wherein the oral dosage form provides a therapeutically effective plasma level of tranexamic acid or pharmaceutically acceptable salt thereof in accordance with a three times a day (TID) dosing schedule, and the therapeutically effective dose administered comprises about 1300 mg of tranexamic acid or pharmaceutically acceptable salt thereof.

In certain preferred embodiments, the invention is further directed to a method of treating a patient with one or more modified release oral dosage forms comprising tranexamic acid or pharmaceutically acceptable salt thereof and a modified release material, wherein the oral dosage form provides a therapeutically effective plasma level of tranexamic acid or pharmaceutically acceptable salt thereof in accordance with a twice a day (BID) dosing schedule, and the therapeutically effective dose administered comprises about 1950 mg of tranexamic acid or pharmaceutically acceptable salt thereof.

In certain embodiments, the invention is directed to a method of providing a tranexamic acid plasma concentration within the range of about 5 mcg/mL to about 15 mcg/mL by administration of a modified release formulation of the present invention comprising tranexamic acid or pharmaceutically acceptable salt thereof and a modified release material on a three times a day basis to a patient in need of tranexamic acid or pharmaceutically acceptable salt thereof treatment.

In certain embodiments, the invention is further directed to a method of treating a human patient with heavy menstrual bleeding (e.g., menorrhagia) comprising administering about 1300 mg of tranexamic acid or pharmaceutically acceptable salt thereof on a three times a day basis to the human patient to provide a tranexamic acid or pharmaceutically acceptable salt thereof plasma concentration within the range of about 5 mcg/mL to about 15 mcg/mL after steady state oral administration to a human patient.

In certain embodiments, the invention is directed to a method of treating a patient suffering from menorrhagia, conization of the cervix, epistaxis, hyphema, hereditary angioneurotic edema, a patient with a blood coagulation disorder undergoing dental surgery, combinations thereof, and the like, by administering at least one dosage form of the present invention to the patient in need in tranexamic acid or pharmaceutically acceptable salt thereof therapy.

In certain embodiments, the invention is directed to a method of treating heavy menstrual bleeding with a therapeutically effective dose of at least one oral formulation of the present invention comprising tranexamic acid or pharmaceutically acceptable salt thereof and a modified release material wherein the menstrual blood loss per menstrual cycle is reduced by at least about 10 ml, preferably at least about 20 ml, more preferably at least about 40 ml. In a most preferred embodiment the menstrual blood loss per menstrual cycle is reduced by greater than or equal to about 50 ml.

In certain embodiments, the invention is directed to a method of treating heavy menstrual bleeding with a therapeutically effective dose of at least one oral formulation of the present invention comprising tranexamic acid or pharmaceutically acceptable salt thereof and a modified release material which upon oral administration to a human female reduces the blood loss per menstrual cycle by about 35 ml to about 200 ml, preferably about 40 ml to about 175 ml, more preferably from about 50 ml to about 150 ml.

In certain embodiments, the invention is further directed to a method of treating heavy menstrual bleeding with a therapeutically effective dose of at least one oral formulation of the present invention comprising tranexamic acid or pharmaceutically acceptable salt thereof and a modified release material which upon oral administration to a human female reduces the blood loss per menstrual cycle by about 20% to 100%, preferably from about 20% to about 70%.

The menstrual blood loss can be measured by procedures known in the art. For example, in certain embodiments, the menstrual blood loss can be determined by a procedure described by (i) L. Hallbert, et al. in "Determination of Menstrual Blood Loss", *Scandinav. J. Clin. & Lab. Investigation*, 244-248, 16, 1964, wherein the procedure is performed by extracting the menstrual blood from vaginal tampons and towels with a sodium hydroxide solution, converting heme chromogens to alkaline hematin, which is determined spectrophotometrically; or (ii) the menstrual blood loss can be determined by a procedure described by J. Newton, M. D., et al., in "A Rapid Method for Measuring Menstrual Blood Loss Using Automatic Extraction.", *Contraception*, 269-282, September 1977, Vol. 16, No. 3, wherein the procedure is based upon the formation of alkaline haematin after the blood has been extracted from vaginal tampons and sanitary towels by an automatic Stomacher Lab-Blender. The disclosures of the aforementioned articles are hereby incorporated by reference in their entireties.

In certain embodiments, the modified release material may be incorporated in a coating applied onto e.g., a tablet comprising the tranexamic acid or pharmaceutically acceptable salt thereof, may be incorporated into a matrix with the tranexamic acid or pharmaceutically acceptable salt thereof, or a combination thereof. For example, in certain preferred embodiments, the modified release material is a controlled release material such as a gel-forming or hydratable polymer which is added to e.g., a matrix composition comprising the tranexamic acid or pharmaceutically acceptable salt thereof.

In certain embodiments, the tranexamic acid for use in the methods and formulations of the present invention is in the form of a pharmaceutically acceptable salt thereof. Such salt forms include for example and without limitation the sodium salt, potassium salt, calcium salt, magnesium salt and the like; as well as the hydrochloride, hydrobromide, sulfate, phosphate, formate, acetate, trifluoroacetate, maleate, tartrate, methanesulfonate, benzenesulfonate, p-toluenesulfonate-methanesulfonate salt forms, and the like. Preferably the active ingredient for use in accordance with the present invention is tranexamic acid.

An "immediate release oral dosage form" for purposes of the present invention is a dosage form which releases all of active ingredient (e.g., tranexamic acid) included therein within about 45 minutes when measured in vitro utilizing the USP 27 Apparatus Type II Paddle Method @ 50 RPM in 900 ml water at 37±0.5° C.

A "modified release oral dosage form" for purposes of the present invention is an oral dosage form which releases the active ingredient (e.g., tranexamic acid) included therein in a manner that is slower than an immediate release oral dosage form and faster than a controlled release oral dosage form, when the dosage forms include the same amount of active as the modified release oral dosage form. One definition of the terms "slower" and "faster" as used in this application is that they are meant to represent a statistically significant difference at each measured 15 minute interval after the start of in-vitro dissolution. In certain preferred embodiments, the modified release oral dosage form of the present invention provides an in-vitro dissolution release rate of tranexamic acid or pharmaceutically acceptable salt thereof, when measured by a USP 27 Apparatus Type II Paddle Method @ 50 RPM in 900 ml water at 37±0.5° C., of less than about 70% by weight tranexamic acid or pharmaceutically acceptable salt thereof released at about 45 minutes and about 100% by weight of said tranexamic acid or pharmaceutically acceptable salt thereof released, by about 120 minutes.

A "controlled release oral dosage form" for purposes of the present invention is a dosage form which releases all of the active ingredient (e.g., tranexamic acid) included therein after about 4 hours or more when measured in vitro utilizing the USP 27 Apparatus Type II Paddle Method @ 50 RPM in 900 ml water at 37±0.5° C.

The term "$C_{max}$" unless otherwise indicated is meant for purposes of the present invention to mean the maximum plasma concentration of a medicament achieved after single dose administration of a dosage form, or the maximum plasma concentration of a medicament achieved over a dosing interval from multiple-doses at steady-state in accordance with the present invention.

The term "$T_{max}$" is meant for purposes of the present invention to mean the elapsed time from administration of a dosage form to the time the $C_{max}$ of the medicament is achieved.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

The term "mean" for purposes of the present invention, when used to define a pharmacokinetic value (e.g., $T_{max}$), unless specified otherwise, represents the arithmetic mean value measured across a patient or subject population.

The term "three times a day (TID) basis" for purposes of the present invention, means that the dosage regimen is to be administered three times a day, preferably on a schedule of every 8 hours.

The term "mean transit time" is understood by those skilled in the art and means the time-point where 63.2% of the total AUC is attained after oral administration, or 63.2% of the IV dose is eliminated, as described in *Applied Pharmacokinetics, Principles of Therapeutic Drug Monitoring*, Second Edition (1986), edited by William E. Evans, et al., the disclosure of which is hereby incorporated by reference in its entirety.

The term "mean absorption time" is understood by those skilled in the art and means a quantitative parameter which summarizes how long, on average, the drug molecule remains unabsorbed, i.e. persists in its dosage form and in the gastrointestinal tract, also as described in *Applied Pharmacokinetics, Principles of Therapeutic Drug Monitoring*, Second Edition (1986), edited by William E. Evans, et al. Unlike the absorption rate constants (ka) which can be skewed, the mean absorption time is not affected by incomplete release of drug from its dosage form, irregular absorption, lag-time, mixed zero-order dissolution rates, changing GI motility, GI blood flow, first-pass effect, etc.

DETAILED DESCRIPTION

Figure 1:
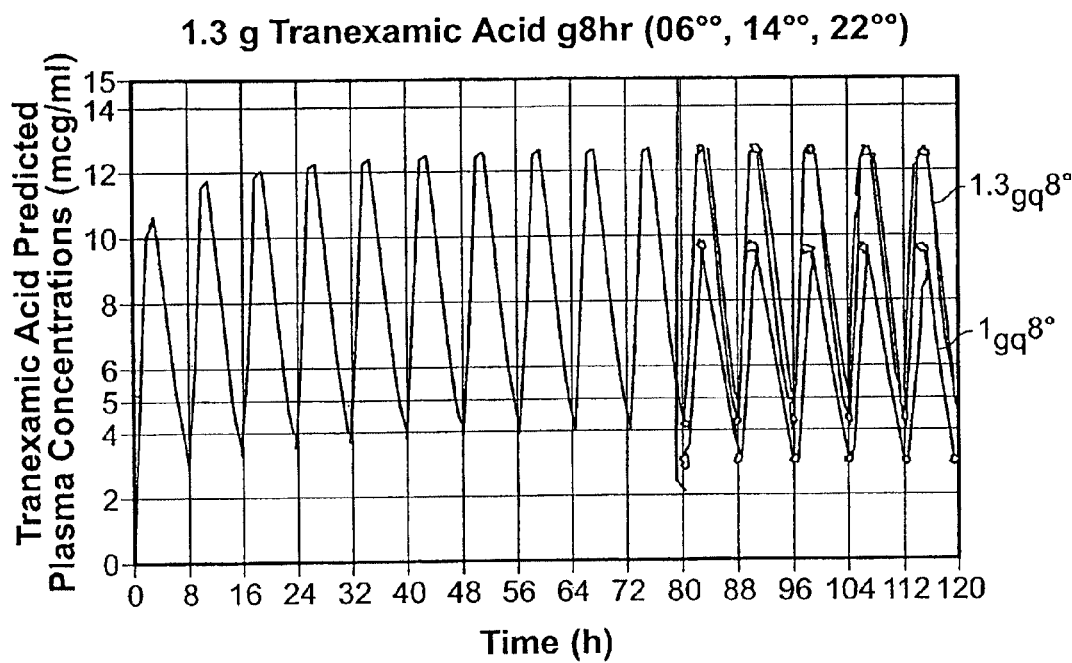
FIG. 1 depicts concentration-time profiles for simulated administration of the 1.3 g tranexamic acid modified release formulation of Example 1 at a Q8H (every 8 hours) dosing schedule of 6:00 AM, 2:00 PM, 10:00 PM comparing it with 1 g administered Q8H.

The dosage regimen typically listed for tranexamic acid in HMB (Heavy Menstrual Bleeding) therapy is 1-1.5 g per dose administered three-four times a day at the onset of copious menstrual bleeding and continued for the first 3-5 days of the menstrual cycle. However, the most frequently reported dosage regimen of tranexamic acid is an immediate release oral formulation in which 1 g tranexamic acid is administered four times a day (4 g per day) for HMB therapy outside of the US. Knowledge of this common regimen is supported by a careful review of the randomized controlled trials published in the medical literature, product labeling from other countries' regulatory authorities having the product approved for HMB therapy, utilization data from Sweden (Rybo 1991), correspondence and interviews with non-US clinicians having experience with the product. That regimen is currently the dosage being studied by the US Center for Disease Control (CDC) in women with HMB associated with bleeding disorders.

The absolute bioavailability of tranexamic acid observed when administering the European commercial formulation (Cyklokapron, Kabi AB, Sweden Batch 90288; assay 499 mgm/tablet) to male subjects is approximately 35% and its elimination correlates with renal creatinine clearance. Peak serum tranexamic acid concentrations occur approximately 3 hours after the oral administration of a European immediate-release tablet formulation (>85% dissolved at 15 minutes) (Pilbrant, et al., *Eur. J. Clin. Pharmacol*, (1981)-20:65-72). By comparison, the in vivo absorption profile observed with the European immediate-release formulation is slow and very gradual over 3 hours. Specifically, tranexamic acid serum concentrations are 9, 41, 73, 88 percent (with food), and 22, 63, 85, and 98 percent (fasting) of maximal absorption at 0.5, 1, 1.5 and 2 hours after a 2 g oral dose, respectively. Although not wishing to be held to any specific theory, it is presently hypothesized that tranexamic acid oral absorption appears to be controlled by a non-dissolution rate limited process, i.e. the rate and extent of oral absorption is a function of a trans-membrane passage-limited process, in order to explain the disparity between the time of product dissolution and relatively prolonged tmax (time to achieve the peak serum concentration).

Preferably, the goal of the formulation, dose strength and dosage regimen of the invention, is to provide HMB therapy which achieves from about 20% to 100% reduction in menstrual blood loss per menstrual cycle. In accordance with certain embodiments of the present invention, the preferred tranexamic acid dose of 1.3 g every 8 hours is predicted to provide an average serum tranexamic acid concentration comparable to that produced by a 1 g every 6 hour regimen (i.e. 12.4 mcg/mL), with associated peaks and troughs falling approximately within the therapeutic antifibrinolytic range (5-15 mcg/mL; Cyklokapron NDA 19-280). In certain embodiments, a two-compartment oral absorption and elimination simulation model coupled with pharmacokinetic data (Pilbrant, et al., *Eur. J. Clin. Pharmacol*, (1981)-20:65-72), and modified-release tablet dissolution performance information were used to determine the preferred lead dosage regimen.

In immediate release formulations the entire dose and the soluble components in the dosage form dissolve in gastrointestinal fluid and present a high concentration of solutes for absorption. The most frequently reported adverse effects are primarily confined to the proximal gastrointestinal tract (nausea and vomiting). These adverse symptoms appear to be related to the drug load presented to the gastric mucosa, since this effect can be minimized by reducing the immediate-release oral formulation dose or administering the product slowly by the intravenous route. In certain embodiments, a lower incidence of proximal gastrointestinal adverse effects is obtained with the preferred oral modified release formulation (e.g., dosed 1.3 g every 8 hours) of the invention, e.g., because of the modified release properties of the drug product formulation.

In certain embodiments, the oral dosage form of the present invention provides for an increased bioavailability as compared to immediate release oral dosage forms currently available (e.g., Cyclokapron). In certain preferred embodiments the increased bioavailability allows therapeutic plasma levels of tranexamic acid to be reached with a lower dose of drug. Preferably, the increased bioavailability also decreases the amount of tranexamic acid that remains unabsorbed in the gastrointestinal which leads to decreased incidence of side effects that are typically associated with formulations that provide higher levels of unabsorbed tranexamic acid and prolonged exposure of the gastrointestinal tract to the higher tranexamic acid levels. Preferably the oral dosage form of the present invention provides for a bioavailability of tranexamic acid of greater than 40%, from about 41% to about 60%, preferably from about 42% to about 50%, more preferably about 45% after oral administration to humans.

The modified release oral formulations of tranexamic acid of the present invention provides a release of the drug which is slower than that of the immediate release 500 mg Cyklokapron product current marketed in Canada which provided a mean release rate of 100% by weight tranexamic acid released by about 15 minutes when measured utilizing USP 27 Apparatus Type II paddle method @ 50 RPM in 900 ml water at 37±0.5° C.

In certain embodiments, the modified release oral formulations may be described as providing a mean transit time through the proximal gastrointestinal mucosa which takes approximately one half hour longer than an immediate release formulation. In other preferred embodiments, the modified release formulations of the invention provide a rate of release of (dissolved) tranexamic acid from the dosage form in-vitro which is approximately 20, 40, 60, 80, and 100 percent of the total dose at 0.25, 0.5, 0.75, 1 and 1.5 hours, respectively. In certain preferred embodiments, such a release rate in-vitro demonstrates that the formulations of the present invention provide a relative reduction in the amount and rate of dissolved tranexamic acid presented to the proximal gastric mucosa to approximate 20, 40, 60, 80, and 100 percent of the total dose at 0.25, 0.5, 0.75, 1 and 1.5 hours, respectively, after oral administration.

In certain embodiments, the majority of tranexamic acid absorption appears to occur slowly distal to the stomach, and assuming linear pharmacokinetics, the modified release formulation produces an absorption profile which is comparable to that achieved with the currently available oral immediate release formulations used outside the U.S.

In accordance with the present invention a modified release tranexamic acid tablet for oral administration is disclosed. Preferably, the tablet contains at least one material (defined herein as any substance other than the active, i.e., tranexamic acid) which minimizes or eliminates the adverse gastrointestinal side effects in patients, for example, women dosed with oral tranexamic acid for treatment of menorrhagia.

The modified release oral dosage forms of tranexamic acid for purposes of the present invention include formulation ingredients and/or configurations which are typically utilized for formulations known in the art as extended, sustained and controlled release formulations, although modified to provide a desirable release rate in keeping with the teachings of the present invention. The modified release formulations preferably decrease the concentration of tranexamic acid and materials dissolved in the stomach fluids after dosing by controllably releasing tranexamic acid over a period of time, as opposed to immediate release formulations which release the entire dose of tranexamic acid all at once. The modified release formulations of the present invention thus minimize or prevent gastrointestinal reactions and side effects that occur when a dose of tranexamic acid is ingested and immediately reaches the stomach.

The modified release dosage forms of the present invention may be prepared as; tablets, capsules, granules, pellets, powders, dragees, troches, non-pariels, pills or encapsulated suspension, and may be packaged into capsules, sachets, etc. Such dosage forms may be prepared by any formulation technique where release of the active substance (tranexamic acid) from the dosage form is modified to occur at a slower rate than from an immediate release product. In these formulations, tranexamic acid release occurs in the stomach and/or intestine, but at a slower rate so that a bolus of dissolved drug does not reach the lining of the stomach and cause adverse effects, or adverse effects occur with a lower intensity or frequency because of the lower concentration of tranexamic acid. Hence, adverse effects are preferably reduced, minimized or eliminated.

Methods of preparing modified release formulations are found in Modified Release Drug Delivery Technology, Rathbone, Hadgraft, and Roberts, Eds., Drugs and the Pharmaceutical Sciences, Vol. 126, Marcel Dekker Inc., New York, 2003; Modern Pharmaceutics, Third Edition, Banker and Rhodes, Eds. Drugs and the Pharmaceutical Sciences, Vol. 72, Marcel Dekker Inc., New York, 1996; Sustained and Controlled Release Drug Delivery Systems, Robinson, Ed., Drugs and the Pharmaceutical Sciences, Vol. 6, Marcel Dekker Inc., NY 1978; Sustained Release Medications, Chemical Technology Review No. 177, Johnson, Ed., Noyes Data Corporation 1980; Controlled Drug Delivery, Fundamentals and Applications, Second Edition, Robinson and Lee, Eds., Marcel Dekker Inc., New York, 1987, and as described in U.S. Pat. No. 6,548,084, each of these references being expressly incorporated by reference herein in its entirety.

Preferably, a modified release form, makes tranexamic acid available over an extended period of time after ingestion. Modified release dosage forms coupled with the digestion process and the absorption process in the gastrointestinal tract cause a reduction in the amount of tranexamic acid in solution in the gastrointestinal tract compared to dosing tranexamic acid presented as a conventional dosage form (e.g., as a solution, or as an immediate release dosage form). The modified release formulation may be verified by in vitro dissolution testing and in vivo bioequivalence documentation, according to Food and Drug Administration standards, e.g., as set forth at www.fda.gov, 21 CFR §314, 320, and also at USP 23 NF 18 §711, 724. For example, an in vitro dissolution test such as USP 27 Apparatus Type II Paddle Method @ 50 RPM in 900 ml water at 37±0.5° C. may be used to verify the release of the tranexamic acid from the dosage form.

Tranexamic acid modified release tablets may be formulated to provide a dose of tranexamic acid, typically about 500 mg to about 2 grams from one to two tablets, within about the first one to two hours after the tablet is ingested. Thus, tranexamic acid release occurs at a designed rate over a period e.g., about 60 minutes to about 120 minutes. The rate of tranexamic acid release over this period of time is designed to provide a reduced concentration of tranexamic acid in the stomach while allowing the absorption of tranexamic acid to occur throughout the gastrointestinal tract. Absorption of tranexamic acid typically begins as soon as tranexamic acid is released from the dosage form and is dissolved in the gastrointestinal fluids contacting the membranes which line the gastrointestinal tract. The rate of release of tranexamic acid from the dosage form and the absorption of drug by the gastrointestinal mucosa help to maintain low concentrations of drug in the gastrointestinal fluids. The lowered concentrations preferably result in lower intensity, frequency, and/or severity of gastrointestinal adverse side effects. The designed rate of release of tranexamic acid from the dosage form in the stomach and the upper small intestine, the natural emptying of gastric juice containing any dissolved tranexamic acid from the stomach, and the absorption of tranexamic acid from a larger segment of the gastrointestinal tract (i.e., both the stomach and the small intestine, rather than the stomach only or the lower portion of the small intestine if any modified release dosage form with a longer release time was used), preferably results in reduced levels of dissolved tranexamic acid in the region of the gastrointestinal tract proximal or distal to the dosage form. Reduced concentrations of tranexamic acid along the gastrointestinal tract preferably provide a reduction in adverse gastrointestinal effects associated with oral tranexamic acid therapy.

As used herein, alleviation of adverse effects using these formulations indicates any relief in one or more symptoms, such as decrease in incidence, severity, or duration of symptoms, and is not limited to absence of symptoms or elimination of symptoms. Thus, treatment includes any decrease in incidence, duration, intensity, frequency, etc. of adverse gastrointestinal symptoms including, but not limited to, headache, nausea, vomiting, diarrhea, constipation, cramping, bloating, and combinations thereof. The formulations may reduce symptoms at any time during tranexamic acid therapy, but minimized adverse effects are particularly noted immediately or shortly after dosing, that is, within the first few hours after dosing. As used herein, adverse gastrointestinal effects and side effects are used interchangeably to indicate nontherapeutic effects (i.e., not relating to any possible beneficial effects due to tranexamic acid), ranging from unpleasant but tolerable sensations to severe gastrointestinal symptoms. As used herein, the terms oral formulations, ingestable formulations, and orally administered formulations are used interchangeably and include any dosage forms which are ingested by mouth, including, but not limited to, tablets, pills, liquids, gelcaps, softgels, dragees, capsules, powders, granules, pellets, etc.

Modified release formulations of tranexamic acid include tablets, pellets, granules, capsules, or other oral dosage forms prepared in such a way to release tranexamic acid in a designed manner. In certain embodiments, the modified release material is a gel-forming polymer, a hydratable polymer, a water soluble polymer, a water swellable polymer, or mixtures thereof.

In certain embodiments, modified release tranexamic acid tablets are prepared by adding a modified release material comprising a gel-forming or hydratable polymer to a tranexamic tablet composition. Suitable gel-forming or hydratable polymers include, but are not limited to, hydroxyproplycellulose, hydroxypropylmethylcellulose or hypromellose, carboxymethylcellulose, polyvinyl alcohol, etc. This provides a compressed tablet that may or may not be film coated. The tablet releases tranexamic acid by diffusion of tranexamic acid through the tablet matrix, or by erosion of the tablet matrix, or by a combination of diffusion from and erosion of the tablet matrix. Tablets formed with water swellable polymers release tranexamic acid by diffusion of tranexamic acid through the tablet matrix, or by erosion of the tablet matrix, or by a combination of diffusion from and erosion of the tablet matrix. One or more water-soluble hydrophilic polymer(s) may also be used. These include polyvinylpyrrolidine, hydroxypropyl cellulose, hydroxypropylmethylcellulose, now referred to as hypromellose (e.g., Methocel™, Dow Chemical Company), methyl cellulose, vinyl acetate/crotonic acid copolymers, methacrylic acid copolymers, maleic anhydride/methyl vinyl ether copolymers, derivatives thereof and mixtures thereof. In various embodiments, the polymer is hydroxypropyl cellulose or hydroxypropylmethylcellulose. The polymer may be hydroxypropyl-methyl cellulose with a viscosity ranging from about 50 cps to about 200 cps. The polymer may be hydroxypropyl-methyl cellulose with a viscosity of 100 cps, commercially available as Methocel™ K 100 LV (Dow Chemical Company). The amount of polymer in the composition may be in the range of about 5% by weight to about 50% by weight of the composition. In various embodiments, the polymer is in the range of about 10% by weight to about 35% by weight of the composition, or about 10% by weight to about 30% by weight of the composition.

In certain embodiments the modified release material comprises a vinyl polymer, phthalic acid derivative of vinyl copolymer, hydroxyalkylcellulose, alkylcellulose (e.g., ethylcellulose), cellulose acetate, hydroxyalkylcellulose acetate, cellulose ether, alkylcellulose acetate and partial esters thereof, and polymers and copolymers of lower alkyl acrylic acids and lower alkyl acrylates and partial esters thereof, or combination thereof. In preferred embodiments the modified release material comprises hydroxypropylcellulose, hydryoxpropylmethylcellulose, carboxymethylcellulose, polyvinyl alcohol, polyvinylpyrrolidone, methylcellulose, vinyl acetate/crotonic acid copolymers, methacrylic acid copolymers, maleic anhydride/methyl vinyl ether copolymers, derivatives thereof, and mixtures thereof. In further preferred embodiments the modified release material comprises a polymer such as a methacrylic acid copolymer. These are copolymers of methacrylic acid with neutral acrylate or methacrylate esters such as ethyl acrylate or methyl methacrylate.

In certain embodiments the modified release material comprises a pH independent binder or film-forming agent such as hydroxypropyl methylcellulose, hydroxypropyl cellulose, methylcellulose, polyvinylpyrrolidone, neutral poly(meth) acrylate esters (e.g., the methyl methacrylate/ethyl acrylate copolymers sold as Eudragit® (Rohm Pharma), starches, gelatin, sugars such as glucose, sucrose, and mannitol, silicic acid, carboxymethylcellulose, and the like, diluents such as lactose, mannitol, dry starch, microcrystalline cellulose and the like, surface active agents, such as polyoxyethylene sorbitan esters, sorbitan ethers, and the like, coloring agents, flavoring agents, lubricants such as talc, calcium stearate, and magnesium stearate, solid polyethylene glycols, sodium lauryl sulfate, and other tableting aids. Any combination of the aforementioned binders or film-forming agents may be included in the modified release material. The modified release material may be combined with tranexamic acid to form modified release dosage forms.

In certain embodiments, the formulation includes tranexamic acid in the range of about 50% by weight to about 95% or more by weight of the formulation. In other embodiments, tranexamic acid is in the range of about 60% by weight to about 90% by weight, or about 60% by weight to about 80% by weight of the formulation. The remaining weight may be made up of the modified release material and additional excipients.

To prepare modified release tablet formulations, the agent or modified release material to slow the release of tranexamic acid may be incorporated into the tablet matrix or coated onto the tablet surface or both. In certain embodiments, tablet formulations prepared are formulated by granulating a blend of powders of the modified release material. The powder blend is formed by combining portions of the powdered components that make up the tablet. These powders are intimately mixed by dry-blending. The dry blended mixture is granulated by wet mixing of a solution of a binding agent with the powder blend. The time for such wet mixing may be controlled to influence the dissolution rate of the formulation. For example, the total powder mix time, that is, the time during which the powder is granulated, may range from about 1 min to about 10 min, or from about 2 min to about 5 min. Following granulation, the particles are removed from the granulator and placed in a fluid bed dryer, a vacuum dryer, a microwave dryer, or a tray dryer for drying. Drying conditions are sufficient to remove unwanted granulating solvent, typically water, or to reduce the amount of granulating solvent to an acceptable level. Drying conditions in a fluid bed dryer or tray dryer are typically about 50 to 70° C. The granulate is dried, screened, mixed with additional excipients such as disintegrating agents, flow agents, or compression aids and lubricants such as talc, stearic acid, or magnesium stearate, and compressed into tablets.

In certain embodiments, the tablet that contains a modified release material within the tablet matrix may be coated with an optional film-forming agent. This applied film may aid in identification, mask an unpleasant taste, allow desired colors and surface appearance, provide enhanced elegance, aid in swallowing, aid in enteric coating, etc. The amount of film-forming agent may be in the range of about 2% tablet weight to about 4% tablet weight. Suitable film-forming agents are known to one skilled in the art and include hydroxypropyl cellulose, cellulose ester, cellulose ether, one or more acrylic polymer(s), hydroxypropyl methylcellulose, cationic methacrylate copolymers (diethylaminoethyl) methacrylate/methyl-butyl-methacrylate copolymers such as Eudragit E® (Rohm Pharma) and the like. The film-forming agents may optionally contain colorants, plasticizers, fillers, etc. including, but not limited to, propylene glycol, sorbitan monooleate, sorbic acid, titanium dioxide, and one or more pharmaceutically acceptable dye(s).

In certain embodiments, the tranexamic acid tablets of the invention are coated with a modified release material. In certain embodiments, tranexamic acid tablets are formulated by dry blending, rotary compacting, or wet granulating powders composed of tranexamic acid and tablet excipients. These powders are compressed into an immediate release tablet. Coating this immediate release tablet with a modified release material as described herein renders this tranexamic acid tablet as a modified release tablet.

In addition to the modified release material, the formulations of the invention may also contain suitable quantities of other materials, e.g. preservatives, diluents (e.g., microcrystalline cellulose), lubricants (e.g., stearic acid, magnesium stearate, and the like), binders (e.g., povidone, starch, and the like), disintegrants (e.g, croscarmellose sodium, corn starch, and the like), glidants (e.g., talc, colloidal silicon dioxide, and the like), granulating aids, colorants, and flavorants that are conventional in the pharmaceutical art. Specific examples of pharmaceutically acceptable excipients that may be used to formulate oral dosage forms are described in the Handbook of Pharmaceutical Excipients, American Pharmaceutical Association (2003), incorporated by reference herein.

The release process may be adjusted by varying the type, amount, and the ratio of the ingredients to produce the desired dissolution profile, as known to one skilled in the art. A coating may be a partially neutralized pH-dependent binder that controls the rate of tranexamic acid dissolution in aqueous media across the range of pH in the stomach, which has a pH of about 2, and the intestine, which has a pH of about 5.5 in its upper region. In certain embodiments, one or more pH dependent binders may be used to modify the dissolution profile so that tranexamic acid is released slowly and continuously as the formulation passes through the stomach and/or intestines.

In one embodiment, compressed modified release tablets are formulated to comply with USP criteria and to be of such a size and shape to be easy to swallow. The size of the tablet will depend upon the dose of tranexamic acid that is needed to provide adequate therapy and the particular formulation and excipients that are selected to provide the physical properties necessary for tableting and for modified release. In various embodiments, a compressed modified release tablet contains from about 500 mg to about 1 gram of tranexamic acid, or from about 600 mg to about 750 mg of tranexamic acid. The daily dose of tranexamic acid may be achieved by taking one or two tablets at each dosing time.

In certain embodiments, the tranexamic acid included in the dosage form is from about 375 mg to about 1500 mg, preferably from about 375 mg to about 1000 mg. In one embodiment, the dose of tranexamic acid per tablet is in the range of about 500 mg to about 1000 mg for tablets and from about 500 mg to about 1500 mg for a sachet filled with granules. In another embodiment, the dose of tranexamic acid is in the range of about 3 grams/day to about 6 grams/day in three or four divided doses. As an example, a total daily dose of 3 grams tranexamic acid may be divided into three doses of one tablet each with each tablet containing 1 gram tranexamic acid, or may be divided into four doses of one tablet each with each tablet containing 0.75 gram tranexamic acid. As another example, a total daily dose of 4 gram tranexamic acid may be divided into three doses of two tablets at each dose with each tablet containing 0.666 gram tranexamic acid, or may be divided into four doses of one tablet each with each tablet containing 1 gram tranexamic acid. As another example, a total daily dose of 5 gram tranexamic acid may be divided into three doses of one tablet each with each tablet containing 1.66 gram tranexamic acid, or may be divided into four doses of two tablets each with each tablet containing 0.625 gram tranexamic acid. As another example, a total daily dose of 6 gram tranexamic acid may be divided into three doses of two tablets each with each tablet containing 1 gram tranexamic acid, or may be divided into four doses of two tablets each with each tablet containing 0.75 gram tranexamic acid. For ease of swallowing, the dose of tranexamic acid taken at each dosing time may be delivered by taking multiple tablets. For example, the 4 gram daily dose may be delivered by taking two 666.67 mg tablets three times a day or two 500 mg tablets four times a day. Similarly, the 3 gram daily dose may be achieved by taking two 550 mg tablets three times a day or two 375 mg tablets four times a day. Alternatively, for ease of reference, a dose of 600 mg, 650 mg, or 700 mg of tranexamic acid per tablet may be used. In a preferred embodiment, a total daily dose of 3900 mg/day is administered in three divided doses of 1300 mg of two tablets at each dose with each tablet containing 650 mg of tranexamic acid. Alternatively, each dose may be delivered by taking granules containing the prescribed amount of tranexamic acid presented in a convenient unit dose package. Such examples are not limiting and other doses within these ranges will be appreciated by those skilled in the art.

Alternatively, modified release tranexamic acid formulations may be administered by pellets or granules in e.g., a sachet or capsule. Modified release tranexamic acid pellets or granules may be prepared by using materials to modify the release of tranexamic acid from the granule or pellet matrix. Modified release preparations may also be formulated using coatings to modify the release of tranexamic acid from the granule or pellet. U.S. Pat. Nos. 5,650,174; and 5,229,135 each of which is expressly incorporated by reference herein in its entirety, disclose variations on fabricating a pellet or nonpareil dosage form. Spheres are filled into packets, termed sachets, or capsules which are filled by weight to contain the prescribed dose of drug. Multiparticulates may be coated with an modified release coating, as disclosed in U.S. Pat. No. 6,066,339, which is expressly incorporated by reference herein its entirety. Coated multiparticulates may be packaged in capsules or sachets. The formulation of granules or pellets for modified release is described in Multiparticulate Oral Drug Delivery, Ghebre-Sellassie, Ed. in Drugs and the Pharmaceutical Sciences, Vol. 65 Marcel Dekker Inc. NY, 1994 and in the relevant parts of the references for modified release formulations previously cited and the relevant portions incorporated herein by reference.

In certain embodiments, the inventive tranexamic acid formulations may be used for additional indications other than menorrhagia, such as conization of the cervix, epistaxis, hyphema, hereditary angioneurotic edema, a patient with a blood coagulation disorder undergoing dental surgery, combinations thereof, and the like.

DETAILED DESCRIPTION OF PREFERRED EMBODIMENTS

The invention will be further appreciated with respect to the following non-limiting examples. Other variations or embodiments of the invention will also be apparent to one of ordinary skill in the art from the above descriptions and examples. Thus, the forgoing embodiments are not to be construed as limiting the scope of this invention.

Example 1

Modified release 650 mg tranexamic acid tablets were prepared having the ingredients listed in the Table 1 below:

TABLE 1

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |

*Purified water is removed during processing

The formulation of Example 1 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the hypromellose USP Methocel K3 Premium to the V-blender. Blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets to desired weight.

Example 2

In Example 2, immediate release 650 mg tranexamic acid tablets were prepared having the ingredients listed in Table 2 below:

TABLE 2

| Ingredient | Quantity per batch (kg) | Quantity per tablet (mg) |
|---|---|---|
| Active Ingredient | | |
| Tranexamic Acid, EP (650 mg/tab) | 84.50 | 650.0 |
| Inactive Ingredients | | |
| Microcrystalline Cellulose, NF (Avicel PH 101) | 5.753 | 44.25 |
| Microcrystalline Cellulose, NF (Avicel PH 102) | 10.660 | 82.00 |
| Colloidal Silicon Dioxide, NF | 0.0975 | 0.75 |
| Pregelatinized Corn Starch, NF | 6.435 | 49.50 |
| Croscarmellose Sodium, NF | 19.50 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water, USP* | 17.550 | 135.00 |
| Film Coating (Inactive Ingredients)** | | |
| Opadry White YS-1-7003 | 4.110 | — |
| Purified Water, USP | 36.990 | — |

*Purified water is removed during processing
**6 kg excess prepared to account for losses during transfer The formulation of Example 2 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets.
12. After compression, spray coat the compressed dosage forms with the Opadry White in water.

Example 3

In Example 3, modified release 650 mg tranexamic acid tablets were prepared as in Example 1 and coated with a film coating similar to the immediate release tablets of Example 2. The ingredients are listed in Table 3 below:

TABLE 3

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |

TABLE 3-continued

| Ingredient | Quantity per batch (kg) | Quantity per tablet (mg) |
|---|---|---|
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |
| Film Coating (Inactive Ingredients)** | | |
| Opadry White YS-1-7003 | 4.305 | — |
| Purified Water, USP | 38.750 | — |

*Purified water is removed during processing
**6 kg excess prepared to account for losses during transfer Example 4

Bioavailability and Bioequivalence Evaluation

In Example 4, a comparative, randomized, single dose, 4-way Crossover Absolute Bioavailability (BA) and Bioequivalence (BE) study of Tranexamic Acid Tablet Formulations prepared in accordance with Examples 1 and 2 in Healthy Adult Women Volunteers under Fasting Conditions was performed. The objective was to assess the bioequivalence of a 650 mg modified release tablet formulation prepared in accordance with Example 1 compared to the immediate release reference tablet formulation of tranexamic acid prepared in accordance with Example 2, and to determine the bioavailability of the modified tablet formulation to the approved IV (1 g) formulation Cyklokapron® by Pharmacia & Upjohn. The design was a randomized, 4-way crossover, comparative BE and BA determination. All oral doses administered were 1.3 g. Twenty-eight (28) healthy non-smoking adult female volunteer subjects were enrolled in the study. Sample size was calculated assuming a 25% CV in $AUC_{inf}$. The study endpoints were the 90% confidence intervals of the ratio of least-squares means of the pharmacokinetic parameters $AUC_{0-t}$, $AUC_{inf}$ and $C_{max}$ of the modified release formulation to the immediate-release formulation from serum concentration-time data drawn up to 36 hours after a single dose of drug. In addition, the bioavailability of the tablet formulations were calculated. Smokers, oral contraceptive users, those with a previous history of thromboembolic events and altered vision were excluded from the study. ECG monitoring was performed before, during and after the estimated times of peak serum tranexamic acid concentrations exposure. Adverse events were captured and recorded throughout the trial period.

In the study, subjects were randomized to receive single oral 1.3 g (2×650 mg tablets) dose of tranexamic acid in tablet forms which included a modified release dosage form and an immediate release dosage form. Subjects were also administered a single 1 g (10 ml) IV solution of tranexamic acid (100 mg/ml concentration).

A summary of the pharmacokinetic results from the study of Example 4 are listed in the tables below.

TABLE 4

Summary of Results—Tranexamic Acid in Plasma Pharmacokinetic Parameters (N = 26)

| | ln AUC 0-t* (mcg • h/mL) | ln AUCinf* (mcg • h/mL) | ln Cmax* (mcg/mL) |
|---|---|---|---|
| Modified Release formulation | | | |
| Mean | 66.703 | 69.642 | 11.251088 |
| CV | 26.8 | 27.2 | 29.1 |
| N | 26 | 24 | 26 |
| Immediate Release formulation | | | |
| Mean | 70.157 | 72.656 | 12.260414 |
| CV | 16.2 | 16.4 | 23.0 |
| N | 26 | 24 | 26 |
| Least-Squares Mean: | | | |
| Modified Release | 66.935 | 68.891 | 11.321919 |
| Immediate Release | 70.051 | 72.411 | 12.258222 |
| Ratio of Least-Squares Mean (modified release/immediate release) % | 95.6 | 95.1 | 92.4 |

*For ln-transformed parameters, the antilog of the mean (i.e. the geometric mean) is reported.
AUCinf, kel, half-life and F could not be estimated for some subjects.
AUC 0-t is the area under the plasma concentration versus time curve, from time 0 to the last measurable concentration, as calculated by the linear trapezoidal method.

TABLE 5

Summary of Results—Tranexamic Acid in Plasma Pharmacokinetic Parameters (N = 26)

| | Tmax (h) | Half-life (h) | kel (1/h) | F (%) |
|---|---|---|---|---|
| Modified Release formulation | | | | |
| Mean | 2.942 | 11.370 | 0.06300 | 44.93 |
| CV | 22.7 | 17.6 | 19.4 | 25.3 |
| n | 26 | 26 | 26 | 24 |
| Immediate Release formulation | | | | |
| Mean | 2.808 | 11.013 | 0.06438 | 46.04 |
| CV | 20.8 | 15.5 | 15.3 | 16.1 |
| n | 26 | 24 | 24 | 24 |

TABLE 6

Summary of Results—Tranexamic Acid in Plasma Pharmacokinetic Parameters (N = 26)

| | Ln AUC 0-t* (mcg • h/mL) | ln AUCinf* (mcg • h/mL) | ln Cmax* (mcg/mL) |
|---|---|---|---|
| 90% Confidence Intervals (Modified release/Immediate release) % | | | |
| lower limit: | 87.8% | 87.4% | 84.0% |
| upper limit: | 104.0% | 103.5% | 101.6% |

TABLE 6-continued

Summary of Results—Tranexamic Acid in Plasma
Pharmacokinetic Parameters
(N = 26)

|  | Ln AUC 0-t* (mcg • h/mL) | ln AUCinf* (mcg • h/mL) | ln Cmax* (mcg/mL) |
|---|---|---|---|
| p-Value (ANOVA) | | | |
| Modified vs Immediate | 0.3721 | 0.3259 | 0.1676 |
| Period | 0.0704 | 0.0499 | 0.0356 |
| Sequence | 0.7734 | 0.7978 | 0.8207 |
| Intrasubject CV % | 18.3 | 17.4 | 20.6 |

*For ln-transformed parameters, the antilog of the mean (i.e. the geometric mean) is reported.
AUCinf, kel, half-life and F could not be estimated for some subjects.

Figure 3:
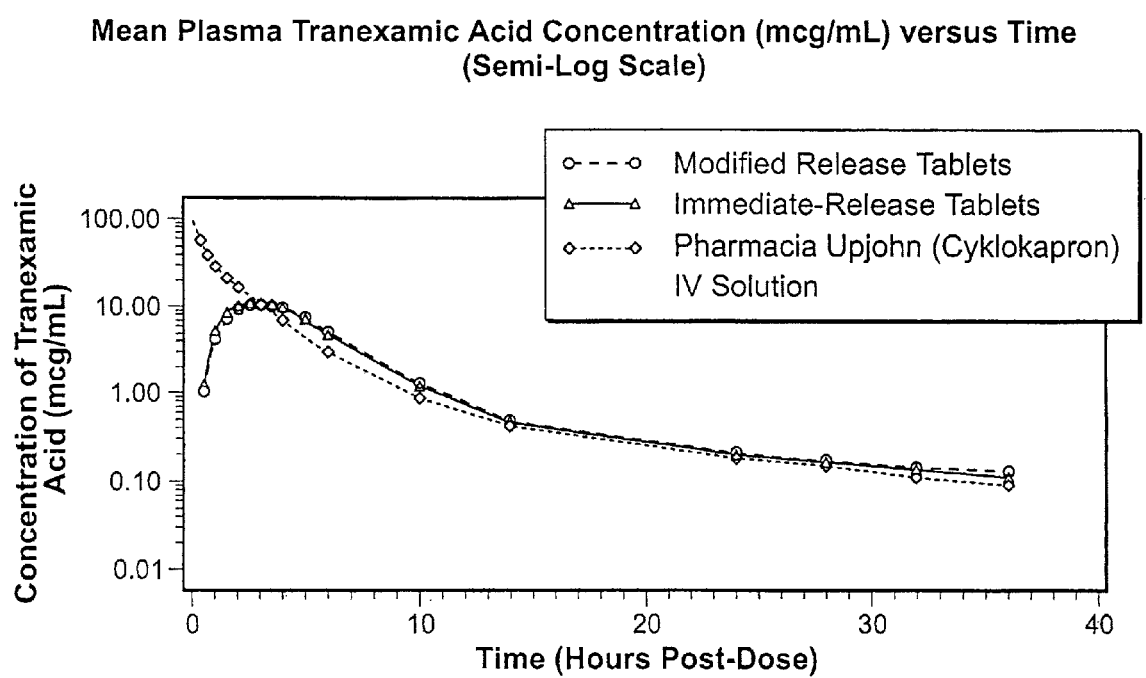
FIG. 3 depicts mean plasma concentration-time profiles on a semi-log scale over 36 hours for the study of Example 4.
Figure 4:
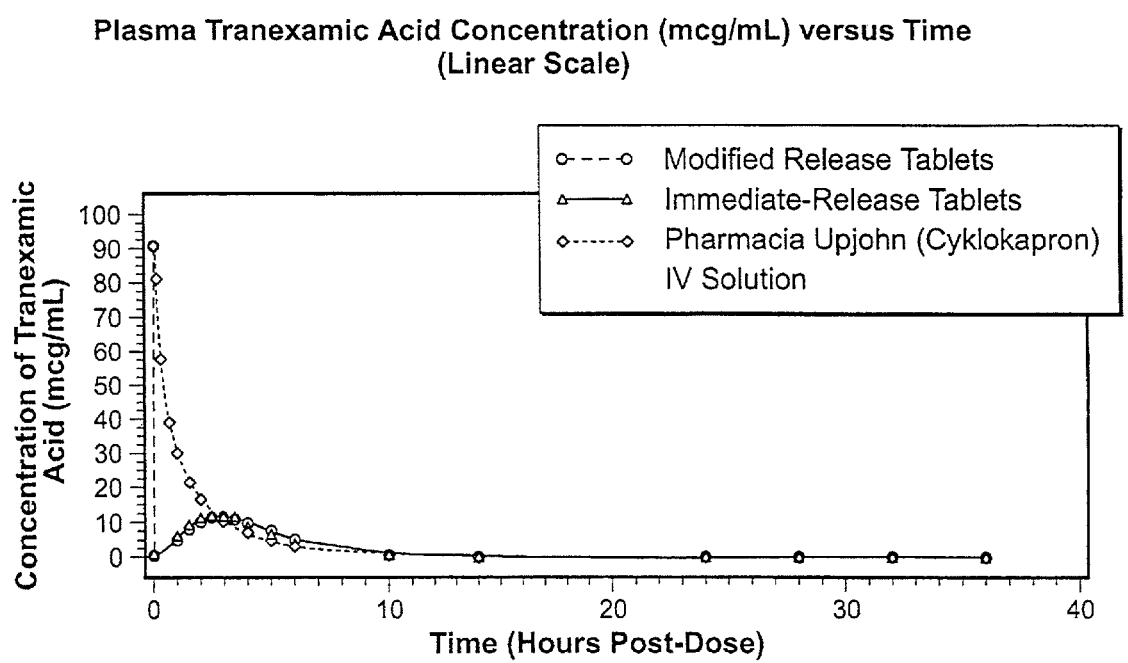
FIG. 4 depicts mean plasma concentration-time profiles on a linear scale over 36 hours for the study of Example 4.

Concentration-time profiles for the study of Example 4 are presented on semi-log and linear scale over 36 hours and are depicted in FIGS. 3 and 4.

The following pharmacokinetic parameters in the table below were calculated for tranexamic acid in plasma for the study of Example 4.

MRT: The mean residence time (MRT) after intravenous administration of tranexamic acid was determined using the equation, AUMC/AUC+infusion time/2, where the AUMC is the area under the moment-time curve.

MTT: Following oral administration of the Modified Release and Immediate Release formulations, the mean transit time (MTT) of tranexamic acid was calculated by dividing the AUMC by the AUC.

MAT: The mean absorption time (MAT) for the two formulations was derived by subtracting the MRT from the MTT.

Mean (±SD) results are presented in the table below:

TABLE 7

|  | IV | Modified Release | Immediate Release |
|---|---|---|---|
| MRT (hours) | 3.51 ± 0.38 | N/A | N/A |
| MTT (hours) | N/A | 7.70 ± 0.72 | 7.21 ± 1.01 |
| MAT (hours) | N/A | 4.18 ± 0.70 | 3.70 ± 0.94 |

The mean transit time (MTT) and mean absorption time (MAT) of the Modified Release formulation of tranexamic acid was approximately 30 minutes longer than that observed for the Immediate Release formulation.

The most frequently reported adverse events from the study of Example 4 are listed in the table below. The table lists the number of subjects reporting adverse events, and the percentage of subjects is in parentheses.

TABLE 8

|  | Treatment | | |
|---|---|---|---|
| Adverse Events | Modified Release (2 × 650 mg) (n = 27) | Immediate Release (2 × 650 mg) (n = 27) | IV solution (10 × 100 mg/ml) (n = 27) |
| Headache | 4 (15%) | 7 (26%) | 7 (26%) |
| Nausea | 0 (0%) | 2 (7%) | 10 (37%) |
| Dizziness | 0 (0%) | 0 (0%) | 11 (41%) |
| Feeling Hot | 0 (0%) | 0 (0%) | 6 (22%) |

TABLE 8-continued

|  | Treatment | | |
|---|---|---|---|
| Adverse Events | Modified Release (2 × 650 mg) (n = 27) | Immediate Release (2 × 650 mg) (n = 27) | IV solution (10 × 100 mg/ml) (n = 27) |
| Nasal Congestion | 2 (7%) | 1 (4%) | 1 (4%) |
| Cough | 0 (0%) | 0 (0%) | 2 (7%) |
| Urine odor abnormal | 2 (7%) | 0 (0%) | 1 (4%) |

Dissolution Results for Immediate Release and Modified Release Formulations prepared in accordance with Examples 2 and 1 respectively used in the study of Example 4 tested under USP 27 Apparatus Type II Paddle Method® 50 RPM in 900 ml water at 37±0.5° C. are listed in the tables below.

TABLE 9

Test Results for the Immediate Release Formulation in Table 2.

|  | % | RSD |
|---|---|---|
| Assay | 99.9% | |
| Content Uniformity | 99.4% | 0.7% |
| Unknown Related Substance | NMT 0.2% Each | <0.1% |
| Total Related Substances and Impurities | NMT 2.0% Total | <0.1% |
| Dissolution Profile | | |
| 15 min. | 58.0% | |
| 30 min. | 96.0% | |
| 45 min. | 102.0% | |
| 60 min. | 104.0% | |

TABLE 10

Test Results for the Modified Release Formulation in Table 1

|  | % | RSD |
|---|---|---|
| Assay | 99.4% | |
| Content Uniformity | 98.5% | 0.6% |
| Unknown Related Substance | NMT 0.2% Each | <0.1% |
| Total Related Substances and Impurities | NMT 2.0% Total | <0.1% |
| Dissolution Profile | | |
| 15 min. | 21.0% | |
| 30 min. | 40.0% | |
| 45 min. | 58.0% | |
| 60 min. | 73.0% | |
| 90 min. | 98.0% | |

Conclusions:

The ratios of least-squares means and the 90% confidence intervals derived from the analyses of the ln-transformed pharmacokinetic parameters $AUC_{0-t}$, $AUC_{inf}$ and $C_{max}$ for tranexamic acid in plasma were within the 80-125% Food and Drug Administration (FDA) acceptance range for the modified release formulation versus the immediate release formulation under fasting conditions.

The absolute bioavailability of the modified release and immediate release tablet formulations were 44.93% and 46.04% respectively.

Based on these results, the modified release tranexamic acid tablet formulation and the immediate release tranexamic acid formulation are bioequivalent under fasting conditions.

Example 4A

Comparative Example

In Comparative Example 4A, a 500 mg immediate release tranexamic acid tablet, approved and marketed in Canada under the name Cyklokapron was obtained and dissolution tested under USP 27 Apparatus Type II Paddle Method @ 50 RPM in 900 ml water at 37±0.5° C. The dissolution results are listed in Table 10A below:

TABLE 10A

| Sample # | % dissolved in 15 min. | % dissolved in 30 min. | % dissolve in 45 min. | % dissolved in 60 min. |
|---|---|---|---|---|
| 1 | 102 | 104 | 105 | 106 |
| 2 | 102 | 104 | 105 | 106 |
| 3 | 101 | 102 | 102 | 105 |
| 4 | 99 | 101 | 102 | 103 |
| 5 | 100 | 102 | 103 | 104 |
| 6 | 99 | 101 | 102 | 104 |
| Average | 101 | 102 | 103 | 105 |
| % RSD | 1.4 | 1.3 | 1.4 | 1.1 |

Example 5

In Example 5, based on single dose pharmacokinetic parameters, pharmacokinetic simulations of serum concentrations were performed to compare dosing the modified release formulation of Example 4 at every 8 hours (Q8H: at 6:00 AM, 2:00 PM, 10:00 PM) and dosing three times a day, other than every 8 hours (TID: at 8:00 AM, 2:00 PM, and 10:00 PM). The results are provided in Tables 11-14 below.

TABLE 11

Tranexamic Acid - Modified Release Formulation
Dosage Regimen Simulation - ORAL 1.3 g q8 hr

| Time (h) | Dose (mcg) | Conc. (mcg/mL) |
|---|---|---|
| 0 | 1.30E+06 | 0 |
| 1 | 0 | 4.0594 |
| 2 | 0 | 10.0551 |
| 3 | 0 | 10.6433 |
| 4 | 0 | 9.20306 |
| 5 | 0 | 7.26932 |
| 6 | 0 | 5.4699 |
| 8 | 1.30E+06 | 2.89909 |
| 9 | 0 | 6.15391 |
| 10 | 0 | 11.5813 |
| 11 | 0 | 11.7752 |
| 12 | 0 | 10.0646 |
| 13 | 0 | 7.94622 |
| 14 | 0 | 6.02067 |
| 15 | 0 | 4.4712 |
| 16 | 1.30E+06 | 3.30248 |
| 17 | 0 | 6.51406 |
| 18 | 0 | 11.9097 |
| 19 | 0 | 12.0794 |
| 20 | 0 | 10.3495 |
| 21 | 0 | 8.21523 |
| 22 | 0 | 6.2761 |
| 23 | 0 | 4.71463 |
| 24 | 1.30E+06 | 3.53505 |
| 25 | 0 | 6.73663 |
| 26 | 0 | 12.1229 |
| 27 | 0 | 12.2838 |
| 28 | 0 | 10.5455 |
| 29 | 0 | 8.40336 |
| 30 | 0 | 6.45664 |
| 31 | 0 | 4.88791 |
| 32 | 1.30E+06 | 3.70138 |

TABLE 11-continued

Tranexamic Acid - Modified Release Formulation
Dosage Regimen Simulation - ORAL 1.3 g q8 hr

| Time (h) | Dose (mcg) | Conc. (mcg/mL) |
|---|---|---|
| 33 | 0 | 6.89628 |
| 34 | 0 | 12.2762 |
| 35 | 0 | 12.4309 |
| 36 | 0 | 10.6868 |
| 37 | 0 | 8.53894 |
| 38 | 0 | 6.5868 |
| 39 | 0 | 5.01286 |
| 40 | 1.30E+06 | 3.82133 |
| 41 | 0 | 7.01144 |
| 42 | 0 | 12.3867 |
| 43 | 0 | 12.537 |
| 44 | 0 | 10.7887 |
| 45 | 0 | 8.63675 |
| 46 | 0 | 6.68069 |
| 47 | 0 | 5.103 |
| 48 | 1.30E+06 | 3.90786 |
| 49 | 0 | 7.09451 |
| 50 | 0 | 12.4665 |
| 51 | 0 | 12.6136 |
| 52 | 0 | 10.8621 |
| 53 | 0 | 8.70731 |
| 54 | 0 | 6.74842 |
| 55 | 0 | 5.16802 |
| 56 | 1.30E+06 | 3.97028 |
| 57 | 0 | 7.15443 |
| 58 | 0 | 12.524 |
| 59 | 0 | 12.6688 |
| 60 | 0 | 10.9152 |
| 61 | 0 | 8.7582 |
| 62 | 0 | 6.79728 |
| 63 | 0 | 5.21493 |
| 64 | 1.30E+06 | 4.01531 |
| 65 | 0 | 7.19766 |
| 66 | 0 | 12.5655 |
| 67 | 0 | 12.7087 |
| 68 | 0 | 10.9534 |
| 69 | 0 | 8.79492 |
| 70 | 0 | 6.83253 |
| 71 | 0 | 5.24877 |
| 72 | 1.30E+06 | 4.0478 |
| 73 | 0 | 7.22885 |
| 74 | 0 | 12.5954 |
| 75 | 0 | 12.7374 |
| 76 | 0 | 10.981 |
| 77 | 0 | 8.82141 |
| 78 | 0 | 6.85796 |
| 79 | 0 | 5.27318 |
| 80 | 1.30E+06 | 4.07124 |
| 81 | 0 | 7.25135 |
| 82 | 0 | 12.617 |
| 83 | 0 | 12.7581 |
| 84 | 0 | 11.0009 |
| 85 | 0 | 8.84052 |
| 86 | 0 | 6.87631 |
| 87 | 0 | 5.29079 |
| 88 | 1.30E+06 | 4.08814 |
| 89 | 0 | 7.26758 |
| 90 | 0 | 12.6326 |
| 91 | 0 | 12.7731 |
| 92 | 0 | 11.0153 |
| 93 | 0 | 8.8543 |
| 94 | 0 | 6.88954 |
| 95 | 0 | 5.3035 |
| 96 | 1.30E+06 | 4.10034 |
| 97 | 0 | 7.27929 |
| 98 | 0 | 12.6439 |
| 99 | 0 | 12.7839 |
| 100 | 0 | 11.0256 |
| 101 | 0 | 8.86425 |
| 102 | 0 | 6.89909 |
| 103 | 0 | 5.31266 |
| 104 | 1.30E+06 | 4.10913 |
| 105 | 0 | 7.28773 |
| 106 | 0 | 12.652 |
| 107 | 0 | 12.7917 |

TABLE 11-continued

Tranexamic Acid - Modified Release Formulation
Dosage Regimen Simulation - ORAL 1.3 g q8 hr

| Time (h) | Dose (mcg) | Conc. (mcg/mL) |
|---|---|---|
| 108 | 0 | 11.0331 |
| 109 | 0 | 8.87142 |
| 110 | 0 | 6.90597 |
| 111 | 0 | 5.31927 |
| 112 | 1.30E+06 | 4.11548 |
| 113 | 0 | 7.29382 |
| 114 | 0 | 12.6578 |
| 115 | 0 | 12.7973 |
| 116 | 0 | 11.0385 |
| 117 | 0 | 8.8766 |
| 118 | 0 | 6.91094 |
| 119 | 0 | 5.32404 |
| 120 | 0 | 4.12006 |

Concentration-time profiles are presented over 120 hours for the modified release formulation in Table 12 and are depicted in FIG. 1. A 1 g formulation administered q8h is also depicted for comparison purposes.

TABLE 12

Cmax, Cmin and Cavg for 1.3 g q8 hr simulation
Simulation at 120 hours

| Pharmacokinetic Parameter | Concentration |
|---|---|
| Cmax | 12.8 mcg/mL |
| Cmin | 4.1 mcg/mL |
| Cavg | 8.4 mcg/ml |

TABLE 13

Tranexamic Acid - Modified Release Formulation
Dosage Regimen Simulation - ORAL
1.3 g TID (8:00 AM, 2:00 PM, and 10:00 PM)

| Time (h) | Dose (mcg) | Conc. (mcg/mL) |
|---|---|---|
| 0 | 1.30E+06 | 0 |
| 1 | 0 | 4.0594 |
| 2 | 0 | 10.0551 |
| 3 | 0 | 10.6433 |
| 4 | 0 | 9.20306 |
| 5 | 0 | 7.26932 |
| 6 | 1.30E+06 | 5.4699 |
| 8 | 0 | 12.9542 |
| 9 | 0 | 12.7378 |
| 10 | 0 | 10.7293 |
| 11 | 0 | 8.40129 |
| 12 | 1.30E+06 | 6.33141 |
| 13 | 0 | 8.74352 |
| 14 | 0 | 13.505 |
| 15 | 0 | 13.2018 |
| 16 | 0 | 11.1327 |
| 17 | 0 | 8.76144 |
| 18 | 0 | 6.65976 |
| 19 | 0 | 4.98823 |
| 20 | 0 | 3.73474 |
| 21 | 0 | 2.8275 |
| 22 | 0 | 2.18502 |
| 23 | 0 | 1.73555 |
| 24 | 1.30E+06 | 1.42243 |
| 25 | 0 | 5.26298 |
| 26 | 0 | 11.104 |
| 27 | 0 | 11.5807 |
| 28 | 0 | 10.058 |
| 29 | 0 | 8.06103 |
| 30 | 1.30E+06 | 6.21137 |
| 31 | 0 | 8.76659 |
| 32 | 0 | 13.6187 |
| 33 | 0 | 13.3709 |
| 34 | 0 | 11.334 |
| 35 | 0 | 8.97998 |
| 36 | 1.30E+06 | 6.88576 |
| 37 | 0 | 9.27495 |
| 38 | 0 | 14.0147 |
| 39 | 0 | 13.6908 |
| 40 | 0 | 11.6019 |
| 41 | 0 | 9.21185 |
| 42 | 0 | 7.09208 |
| 43 | 0 | 5.40321 |
| 44 | 0 | 4.1331 |
| 45 | 0 | 3.20991 |
| 46 | 0 | 2.55212 |
| 47 | 0 | 2.08796 |
| 48 | 1.30E+06 | 1.76074 |
| 49 | 0 | 5.58776 |
| 50 | 0 | 11.4158 |
| 51 | 0 | 11.88 |
| 52 | 0 | 10.3453 |
| 53 | 0 | 8.33688 |
| 54 | 1.30E+06 | 6.47618 |
| 55 | 0 | 9.02081 |
| 56 | 0 | 13.8627 |
| 57 | 0 | 13.6052 |
| 58 | 0 | 11.5589 |
| 59 | 0 | 9.1959 |
| 60 | 1.30E+06 | 7.09304 |
| 61 | 0 | 9.47395 |
| 62 | 0 | 14.2057 |
| 63 | 0 | 13.8742 |
| 64 | 0 | 11.778 |
| 65 | 0 | 9.38036 |
| 66 | 0 | 7.25433 |
| 67 | 0 | 5.55898 |
| 68 | 0 | 4.28264 |
| 69 | 0 | 3.35346 |
| 70 | 0 | 2.68993 |
| 71 | 0 | 2.22026 |
| 72 | 1.30E+06 | 1.88775 |
| 73 | 0 | 5.70968 |
| 74 | 0 | 11.5329 |
| 75 | 0 | 11.9924 |
| 76 | 0 | 10.4532 |
| 77 | 0 | 8.44044 |
| 78 | 1.30E+06 | 6.57559 |
| 79 | 0 | 9.11625 |
| 80 | 0 | 13.9543 |
| 81 | 0 | 13.6931 |
| 82 | 0 | 11.6434 |
| 83 | 0 | 9.27696 |
| 84 | 1.30E+06 | 7.17086 |
| 85 | 0 | 9.54865 |
| 86 | 0 | 14.2775 |
| 87 | 0 | 13.943 |
| 88 | 0 | 11.8441 |
| 89 | 0 | 9.44431 |
| 90 | 0 | 7.31525 |
| 91 | 0 | 5.61745 |
| 92 | 0 | 4.33877 |
| 93 | 0 | 3.40735 |
| 94 | 0 | 2.74167 |
| 95 | 0 | 2.26992 |
| 96 | 1.30E+06 | 1.93543 |
| 97 | 0 | 5.75546 |
| 98 | 0 | 11.5768 |
| 99 | 0 | 12.0346 |
| 100 | 0 | 10.4937 |
| 101 | 0 | 8.47931 |
| 102 | 1.30E+06 | 6.61292 |
| 103 | 0 | 9.15208 |
| 104 | 0 | 13.9887 |
| 105 | 0 | 13.7261 |
| 106 | 0 | 11.6751 |

TABLE 13-continued

Tranexamic Acid - Modified Release Formulation
Dosage Regimen Simulation - ORAL
1.3 g TID (8:00 AM, 2:00 PM, and 10:00 PM)

| Time (h) | Dose (mcg) | Conc. (mcg/mL) |
|---|---|---|
| 107 | 0 | 9.30739 |
| 108 | 1.30E+06 | 7.20008 |
| 109 | 0 | 9.5767 |
| 110 | 0 | 14.3044 |
| 111 | 0 | 13.9689 |
| 112 | 0 | 11.8689 |
| 113 | 0 | 9.46813 |
| 114 | 0 | 7.33811 |
| 115 | 0 | 5.63941 |
| 116 | 0 | 4.35985 |
| 117 | 0 | 3.42759 |
| 118 | 0 | 2.76109 |
| 119 | 0 | 2.28857 |
| 120 | 0 | 1.95333 |

Figure 2:
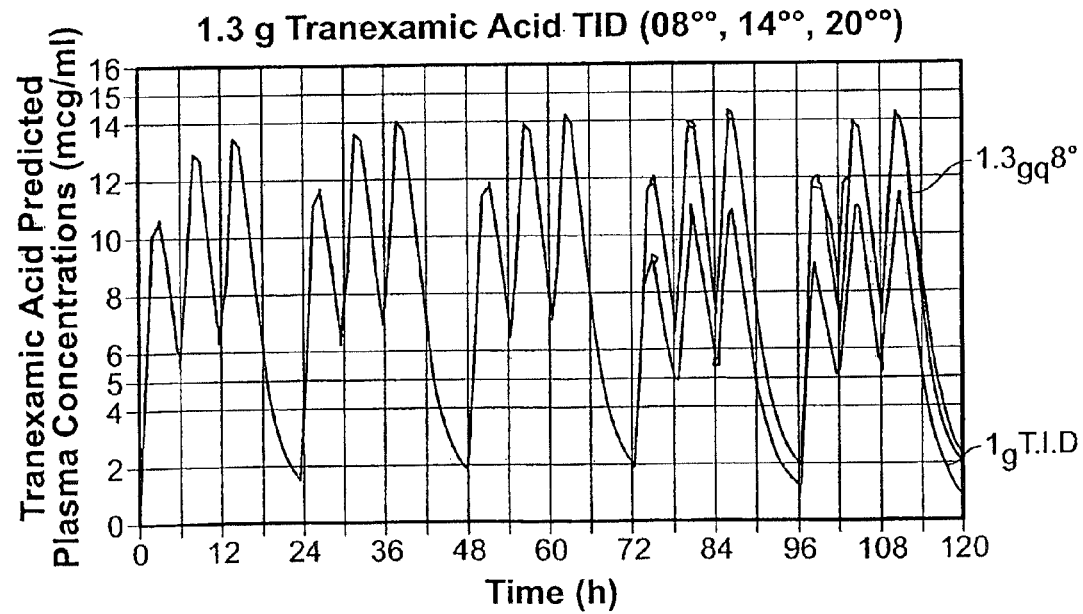
FIG. 2 depicts concentration-time profiles for simulated administration of the 1.3 g tranexamic acid modified release formulation of Example 1 at a TID (three times a day) dosing schedule of 8:00 AM, 2:00 PM, 8:00 PM comparing it with 1 g administered TID.

Concentration-time profiles are presented over 120 hours for the modified release formulation in Table 14 and are depicted in FIG. 2. A 1 g formulation administered TID is also depicted for comparison purposes.

TABLE 14

Cmax, Cmin and Cavg for 1.3 g TID (8:00 AM, 2:00 PM, and 10:00 PM)
Simulation at 120 hours

| Pharmacokinetic Parameter | Conc. |
|---|---|
| Cmax | 12.0, 14.0, 14.3 mcg/mL |
| Cmin | 1.9, 6.6, 7.2 mcg/mL |
| Cavg | 8.4 mcg/mL |

Example 6

In Example 6, a study of a single dose followed by multiple doses, was performed on 20 healthy non-smoking adult female volunteers using a modified release formulation prepared in accordance with Example 1. After an overnight fast, subjects received a single oral dose of tranexamic acid (1.3 g) on Day 1. Blood samples were taken before dosing and up to 36 hours post-dose. Subjects received another single oral dose of tranexamic acid (1.3 g) on the evening of Day 2, and 3 times a day (every 8 hours) starting on the morning of Day 3 until the last dose on the morning of Day 7. Blood samples were taken before the 6th, 9th, 12th and 15th dose (the last dose) for the determination of $C_{min}$, and up to 8 hours after the last dose, for the determination of drug concentration at steady-state. Subjects were housed from at least 10 hours before the 1st dose on Day 1 until after the 8-hour blood draw following the 15th dose (on Day 7).

Tranexamic acid is minimally bound (approximately 3%) to plasma proteins (mainly plasminogen) at "typical" therapeutic plasma concentrations of approximately 5-15 mg/L. The main route of elimination of tranexamic acid is renal glomerular filtration. After oral administration of tranexamic acid (250 or 500 mg) to healthy adults, between 40-70% of the administered dose is excreted unchanged in the urine within 24 hours. After IV administration (1 g) 30% of the dose is excreted unchanged in the urine within one hour, 45-55% within 2-3 hours and 90% within 24 hours.

The beta elimination half-life of tranexamic acid is 2 hours. Based on published data, the mean $C_{max}$ and $AUC_{0-6}$ pharmacokinetic parameters after a single 1.3 g oral dose of tranexamic acid are expected to be approximately 65% of those achieved with a 2 g dose (i.e. ~10 mg/L and ~40 mg-h/L, $C_{max}$ and $AUC_{0-6}$ under fasting conditions, respectively).

However, the pharmacokinetics of tranexamic acid were not adequately characterized in Pilbrant, et al., *Eur. J. Clin. Pharmacol*, (1981)-20:65-72, since blood samples were collected for up to only 6 hours post-dose. In addition, the plasma concentration-time curves after IV administration showed three exponential phases, with a gamma elimination half-life of approximately 7 hours. For this reason, the concentration-time profile of tranexamic acid was estimated by simulating the data over 36 hours, after oral administration of a 1.3 g dose under fasting conditions, using NONMEM. Based on the simulation results, it would be appropriate to collect blood samples until 36 hours in order to characterize the AUC, Cmax, tmax, t½ and F.

The objective of this study of Example 6 was to assess the pharmacokinetic linearity of the test tablet formulation of tranexamic acid (modified release), after a single oral dose (Day 1) compared to a daily (1.3 g every 8 hours) dosage regimen (Days 2 to 7), under fasting conditions.

In the study of Example 6, blood samples (1×5 mL) were collected in blood collection tubes containing lithium heparin at Hour 0 (pre-dose) on Day 1, and at 0.5, 1, 1.5, 2, 2.5, 3, 3.5, 4, 5, 6, 8, 10, 14, 24, 28, 32, and 36 hours post-dose. Blood samples for Cmin determinations were also collected immediately before the 6th, 9th, 12th, and 15th doses on Days 4, 5, 6, and 7, respectively, and at the following times after the 15th dose: 0.5, 1, 1.5, 2, 2.5, 3, 3.5, 4, 5, 6, and 8 hours. Plasma samples were separated by centrifugation, then frozen at −20° C.±10° C. and kept frozen until assayed at AAI Development Services in New-Ulm, Germany.

Noncompartmental Pharmacokinetic Parameters

Calculations for plasma tranexamic acid were calculated by noncompartmental methods using the following pharmacokinetic parameters in Tables 15 and 16:

Day 1:

TABLE 15

| | |
|---|---|
| AUC 0-t: | The area under the plasma concentration versus time curve, from time 0 to the last measurable concentration, as calculated by the linear trapezoidal method. |
| AUCinf: | The area under the plasma concentration versus time curve from time 0 to infinity. AUCinf was calculated as the sum of AUC 0-t plus the ratio of the last measurable plasma concentration to the elimination rate constant. |
| AUC/ AUCinf: | The ratio of AUC 0-t to AUCinf. |
| Cmax: | Maximum measured plasma concentration over the time span specified. |
| tmax: | Time of the maximum measured plasma concentration. If the maximum value occured at more than one time point, tmax was defined as the first time point with this value. |
| kel: | Apparent first-order terminal elimination rate constant calculated from a semi-log plot of the plasma concentration versus time curve. This parameter was calculated by linear least squares regression analysis using the maximum number of points in the terminal log-linear phase (e.g. three or more non-zero plasma concentrations). |
| t½: | The apparent first-order terminal elimination half-life was calculated as 0.693/kel. |

No value for kel, AUCinf or t½ were reported for cases that did not exhibit a terminal log-linear phase in the concentration versus time profile.

Day 7:

TABLE 16

| | |
|---|---|
| AUCτ: | The area under the plasma concentration versus time curve over the final dosing interval, as calculated by the linear trapezoidal method. |
| Cmax: | Maximum measured plasma concentration over the final dosing interval. |
| Cmin: | Measured plasma concentration prior to the morning dose. |
| tmax: | Time of the maximum measured plasma concentration over the final dosing interval. If the maximum value occured at more than one time point, tmax was defined as the first time point with this value. |
| Flux: | Percent fluctuation was calculated as follows: Flux 1: $$\frac{Cmax - Cmin}{Cssav} \times 100$$ where Cssav was calculated as the ratio of AUC 0-τ to the dosing interval, τ. Flux 2: $$\frac{Cmax - Cmin}{Cmin} \times 100$$ |

Compartmental Pharmacokinetic Parameters

Compartmental analysis was performed on tranexamic acid data following single and multiple oral administrations of the modified release (MR) tablet formulation. Multiple compartmental models were constructed and their ability to fit plasma concentrations of tranexamic acid were evaluated using a standard two-stage (STS) approach with ADAPT-II (maximum likelihood analysis). The discrimination process was performed by computing the Akaike Information Criterion Test (AIC), the minimum value of the objective function (OBJ) and by looking at pertinent graphical representations of goodness of fit (e.g. fitted and observed concentrations versus time).

The final analysis was performed using an iterative two-stage approach with the IT2S® software. This software uses a population methodology which allows one to provide robust PK parameter estimates on an individual subject and population basis. All relevant pharmacokinetic parameters were calculated and reported. Concentrations were modeled using a weighting procedure of $W_j = 1/S_j^2$ where the variance $\sigma j^2$ was calculated for each observation using the equation $\sigma j^2 = (a \pm b^* Y_j)^2$ where a and b are the intercept and slope of each variance model. The slope is the residual variability associated with each concentration (includes the intra-individual variability and the sum of all experimental errors), and the intercept is related to the limit of detection of the analytical assay. All PK parameter estimates were updated iteratively during the population PK analysis (VARUP, IT2S®) until stable values were found. The analysis included the quantitative estimation of population PK parameters and interindividual variability of tranexamic acid in plasma.

Individual profiles of observed vs fitted plasma concentrations of tranexamic acid were provided for the MR formulation.

Statistical Analyses
Descriptive Statistics

Descriptive statistics including arithmetic means, standard deviations and coefficients of variation were calculated on the individual concentration and pharmacokinetic data. Additionally, geometric means were calculated for the parameters $AUC_{0-\tau}$, $AUC_{inf}$ and $C_{max}$ for Day 1 and $AUC\tau$, $C_{max}$ and $C_{min}$ for Day 7.

Time Dependence Pharmacokinetic Linearity

The pharmacokinetic parameter AUCτ (Day 7) was compared against $AUC_{inf}$ (Day 1) using an analysis of variance (ANOVA) on the ln-transformed values for tranexamic acid. The ANOVA model included Group, Day (1 ($AUC_{inf}$) and 7 (AUCτ)) and the interaction Day*Group as fixed effects. All the interaction terms were not statistically significant, at a level of 5%, and were dropped from the final model. The ANOVA included calculation of least-squares means (LSM), the difference between Day LSM and the standard error associated with this difference. The above statistical analysis was done using the SAS® GLM procedure.

The ratio of LSM was calculated using the exponentiation of the Day LSM from the analysis on the ln-transformed response. The ratio was expressed as a percentage relative to $AUC_{inf}$ (Day 1).

A ninety percent confidence interval for the ratio was derived by exponentiation of the confidence interval obtained for the difference between Day LSM resulting from the analysis on the ln-transformed response. The confidence interval was expressed as a percentage relative to $AUC_{inf}$ (Day 1).

Steady-State Analysis

A steady-state analysis was performed, on the ln-transformed pre-dose Cmin concentrations at −72, −48, −24 and 0-hour time points, using Helmert's contrasts. The ANOVA model included Group, Time and the interaction Time*Group as fixed effects. In order to model the correlations within every subject, an appropriate variance-covariance matrix was chosen among the following: unstructured (UN), compound symmetry (CS), compound symmetry heterogeneous (CSH), variance component (VC), autoregressive (AR(1)), autoregressive heterogeneous (ARH(1)) and autoregressive moving average (ARMA(1,1)), using the Akaike's Burnham and Anderson criterion (AICC). All the interaction terms were not statistically significant, at a level of 5%, and were dropped from the final model. The ANOVA included also calculation of least-squares means (LSM) for each pre-dose $C_{min}$ concentrations. Helmert's contrasts were constructed such that each time point is compared to the mean of subsequent time points. There are 3 contrasts associated to the 4 pre-dose concentration timepoints. They are listed in Table 17 below:

TABLE 17

| Contrast | Tests |
|---|---|
| Compar. 1 | Predose Day 4 compared to (mean predose of Day 5, 6 and 7) |
| Compar. 2 | Predose Day 5 compared to (mean predose of Day 6 and 7) |
| Compar. 3 | Predose Day 6 compared to predose Day 7 (0-hour) |

The above statistical analyses were done using the SAS® Mixed procedure.

Formulae

The following formulae in Table 18 were used for the ratio of least-squares means and 90% confidence interval calculations derived from the ANOVA on the ln transformed pharmacokinetic parameters.

TABLE 18

| | |
|---|---|
| Ratio of Least-squares Means: | $100 \times e^{(LSM_{Day\ 7} - LSM_{Day\ 1})}$ |
| 90% Confidence Interval: | $100 \times e^{(LSM_{Day\ 7} - LSM_{Day\ 1} \pm t_{df, 0.05} \times SE_{Day\ 7-Day\ 1})}$ |

Note:

$LSM_{Day\ 7}$ and $LSM_{Day\ 1}$ are the least-squares means of Day 7 and Day 1, as computed by the LSMEANS statement of the SAS ® GLM procedure.

$t_{df,\alpha}$ is the value of the Student's t distribution with df degrees of freedom (i.e. degrees of freedom for the error term from the analysis of variance) and a right-tail fractional area of α (α = 0.05).

$SE_{Day7-Day1}$ is the standard error of the difference between the adjusted Day means, as computed by the ESTIMATE statement in the SAS ® GLM procedure.

Discussion of Pharmacokinetic Results

Time Dependence Pharmacokinetic Linearity

The ANOVA model included Group, Day (1 ($AUC_{inf}$) and 7 (AUCτ)) and the interaction Day*Group as the fixed effect. All the interaction terms were not statistically significant, at a level of 5%, and were dropped from the final model. Pharmacokinetic linearity was calculated for the formulation using the same approach as above, but the ANOVA model included Group, Day 1 (AUCinf) and Day 7 (AUCτ)) and the interactions Group*Day as fixed effects and Subject nested within Group as a random effect.

The pharmacokinetic linearity results are summarized in the table below.

TABLE 19

| | | 90% Confidence Interval | |
|---|---|---|---|
| Formulation | Ratio AUCτ/AUCinf | Lower Limit | Upper Limit |
| MR | 97.3 | 86.5 | 109.5 |

The pharmacokinetic linearity results indicate that the ratios of least-squares means of AUCτ (Day 7) to $AUC_{inf}$ (Day 1) and the 90% confidence interval for the MR formulation were within the 80-125% acceptance range. Based on these results, the 650 mg tranexamic acid modified release tablets exhibited linear pharmacokinetics following repeated administration (7 days) of a 1.3 g dose under fasting conditions.

Steady-State Analysis

For the steady-state analysis, the CS variance-covariance matrix was chosen to model the correlations within every subject. Overall, the interaction term (i.e. Time*Group) was not statistically significant and was removed from the final ANOVA model. For each formulation, the same approach as above was used, but the ANOVA models included Group, Time and the interactions Time*Group as fixed effects.

A summary of LSM results for the steady-state analysis are summarized in Table 20A below.

TABLE 20A

| Formulation | Days | Times (hour) | LSM derived from the ANOVA |
|---|---|---|---|
| MR | 4 | −72 | 4.90536 |
| | 5 | −48 | 4.77323 |
| | 6 | −24 | 5.23678 |
| | 7 | 0 | 5.15389 |

Summary of statistical comparisons for the steady-state analysis are summarized in Table 20B below

TABLE 20B

| Formulation | Helmert's contrasts | P-value |
|---|---|---|
| MR | Predose Day 4 compared to (mean predose of Day 5, 6 and 7) | 0.4438 |
| | Predose Day 5 compared to (mean predose of Day 6 and 7) | 0.0393 |
| | Predose Day 6 compared to predose Day 7 | 0.7318 |

Based on the results above, steady-state plasma concentration of tranexamic acid were reached on Day 4 (−72-hour), since the p value for the first contrast was not statistically significant at a 5% alpha error. It should be noted that the second comparison [Predose Day 5 compared to (mean of Day 6 and 7)] was found to be statistically significant.

The largest difference observed in predose plasma concentrations of tranexamic acid between the LSM of predose Day 5 compared to Day 6 and 7 was less than 10%, which is not considered clinically relevant. Moreover, the last contrast was not statistically significant and the observed difference between the LSM of predose Day 6 and 7 was less than 2%.

Compartmental Pharmacokinetic Analysis

The mean apparent oral clearance (CL/F) of the MR formulation calculated with compartmental methods was 17.7 L/h (295 mL/min). Based on previous data reported in the literature, the group of Pilbrant, et al., have determined that the urinary recovery of tranexamic acid exceeded 95% of the dose administered. Considering the bioavailability of the MR formulation (Mean F: 44.9%, See Table 5), the systemic clearance (CL) of tranexamic acid (295 mL/min×0.449=123 mL/min) would be close to the glomerular filtration rate in healthy subjects (125 mL/min)5.

Using compartmental methods, the mean T½γ for the MR formulation was 16.6 hours. Similar values of terminal elimination half-life were previously reported in the literature. Pilbrant A., et al., Eur. J. Clin. Pharmacol (1981), 20: 65-72.

Following a single oral dose of 1.3 g of the MR formulation, the mean plasma concentrations of tranexamic acid observed at 28, 32, and 36 hours were 0.19724, 0.15672, and 0.13624 mcg/mL, respectively. Considering the therapeutic window of tranexamic acid (5-15 mcg/mL) and the very low plasma concentration levels observed at these timepoints, the terminal elimination half-life (T½γ) characterizing the slow decline of plasma concentrations should not play a clinically significant role in the frequency of drug administration.

Pharmacokinetic Conclusions

The pharmacokinetic linearity results indicate that the ratios of least-squares means of AUCτ (Day 7) to AUCinf (Day 1) and the 90% confidence interval for the MR formulation were within the 80-125% acceptance range. Based on these results, the 650 mg tranexamic acid modified release tablets exhibited linear pharmacokinetics following repeated administration (7 days) of a 1.3 g dose under fasting conditions.

Steady-state plasma concentrations of tranexamic acid for the modified-release tablets were reached on Day 4 (−72-hour), since the p-value for the first contrast was not statistically significant at a 5% alpha error.

The pharmacokinetics of tranexamic acid was properly described using a three compartment PK model with linear elimination. The absorption kinetic of the single-dose (Day 1) data of tranexamic acid for the MR formulation was best described using a mixed-order rate constant of absorption.

Plasma Pharmacokinetic Parameters for the modified release (MR) formulation of Tranexamic Acid on day 1 are listed in Table 21 below.

TABLE 21

|  | In AUC$_{0-t}$* (mcg·h/ml) | In AUC$_{inf}$* (mcg·h/ml) | In C$_{max}$* (mcg/ml) | T$_{max}$ (h) | Half-life (h) | K$_{el}$ (1/h) |
|---|---|---|---|---|---|---|
| Mean | 74.571 | 76.875 | 13.176041 | 3.079 | 11.078 | 0.06443 |
| CV % | 31.3 | 30.4 | 33.1 | 25.0 | 16.9 | 18.3 |
| N | 19 | 19 | 19 | 19 | 19 | 19 |

*For ln-transformed parameters, the antilog of the mean (i.e. the geometric mean) is reported;
AUC$_{0-t}$ = AUC post dose (0-36 hours)

Plasma Pharmacokinetic Parameters for the modified release (MR) formulation of Tranexamic Acid on day 7 are listed in Table 22 below.

TABLE 22

|  | In AUC$_\tau$* (mcg·h/ml) | In C$_{max}$* (mcg/mL) | In C$_{min}$* (mcg/ml) | T$_{max}$ (h) | Flux 1** (%) | Flux 2** (%) |
|---|---|---|---|---|---|---|
| Mean | 74.791 | 15.803509 | 5.157681 | 2.553 | 113.16 | 219.21 |
| CV % | 29.0 | 30.1 | 31.2 | 14.4 | 21.6 | 44.6 |
| N | 19 | 19 | 19 | 19 | 19 | 19 |

*For ln-transformed parameters, the antilog of the mean (i.e. the geometric mean) is reported;
AUC$_\tau$ = AUC dosing interval (8 hours)
**Defined in Table 16

CONCLUSION

While the invention herein disclosed has been described by means of specific embodiments and applications thereof, numerous modifications and variations could be made thereto by those skilled in the art without departing from the spirit and scope of the present invention. Such modifications are understood to be within the scope of the appended claims.

What is claimed is:

1. A tranexamic acid tablet formulation comprising:
   tranexamic acid or a pharmaceutically acceptable salt thereof; and
   a modified release material;
   wherein the tranexamic acid or pharmaceutically acceptable salt thereof is present in an amount from about 50% to about 95% by weight of the formulation;
   wherein the modified release material is present in an amount from about 5% to about 50% by weight of the formulation; and
   wherein said tablet formulation provides an in-vitro dissolution release rate of the tranexamic acid or pharmaceutically acceptable salt thereof, when measured by a USP 27 Apparatus Type II Paddle Method @ 50 RPM in 900 ml water at 37±0.5° C., of less than about 40% by weight of the tranexamic acid or pharmaceutically acceptable salt thereof released at about 15 minutes, and not less than about 50% by weight of the tranexamic acid or pharmaceutically acceptable salt thereof released at about 90 minutes.

2. The tranexamic acid tablet formulation of claim 1, wherein said tablet formulation provides an in-vitro dissolution release rate of the tranexamic acid or pharmaceutically acceptable salt thereof, when measured by a USP 27 Apparatus Type II Paddle Method @ 50 RPM in 900 ml water at 37±0.5° C., of less than about 40% by weight of the tranexamic acid or pharmaceutically acceptable salt thereof released at about 15 minutes, less than about 70% by weight of the tranexamic acid or pharmaceutically acceptable salt thereof released at about 45 minutes, and not less than about 50% by weight of the tranexamic acid or pharmaceutically acceptable salt thereof released at about 90 minutes.

3. The tranexamic acid tablet formulation of claim 1, wherein said formulation provides an in-vitro dissolution release rate of the tranexamic acid or pharmaceutically acceptable salt thereof, when measured by the USP 27 Apparatus Type II Paddle Method @ 50 RPM in 900 ml water at 37±0.5° C., of about 0% to about 40% by weight of the tranexamic acid or pharmaceutically acceptable salt thereof released at about 15 minutes, from about 20% to about 60% by weight of the tranexamic acid or pharmaceutically acceptable salt thereof released at about 30 minutes, from about 40% to about 65% by weight of the tranexamic acid or pharmaceutically acceptable salt thereof released at about 45 minutes, from about 50% to about 95% by weight of the tranexamic acid or pharmaceutically acceptable salt thereof released at about 60 minutes, and not less than about 60% by weight of the tranexamic acid or pharmaceutically acceptable salt thereof released at about 90 minutes.

4. The tranexamic acid tablet formulation of claim 1, wherein the tranexamic acid or pharmaceutically acceptable salt thereof is tranexamic acid.

5. The tranexamic acid tablet formulation of claim 1, wherein formulation provides a dose of about 650 mg of tranexamic acid per tablet.

6. The tranexamic acid tablet formulation of claim 5, wherein the tranexamic acid or pharmaceutically acceptable salt thereof is tranexamic acid.

7. The tranexamic acid tablet formulation of claim 1, wherein the modified release material comprises hydroxypropylmethylcellulose.

8. The tranexamic acid tablet formulation of claim 7, wherein formulation provides a dose of about 650 mg of tranexamic acid per tablet.

9. The tranexamic acid tablet formulation of claim 8, wherein the tranexamic acid or pharmaceutically acceptable salt thereof is tranexamic acid.

10. The tranexamic acid tablet formulation of claim 1, wherein the formulation is in the form of a matrix tablet which comprises a drug mixed together with a granulated modified release material.

11. The tranexamic acid tablet formulation of claim 10, wherein the formulation provides a dose of about 650 mg of tranexamic acid per tablet.

12. The tranexamic acid tablet formulation of claim 11, wherein the tranexamic acid or pharmaceutically acceptable salt thereof is tranexamic acid.

13. The tranexamic acid tablet formulation of claim 1, wherein the tranexamic acid or pharmaceutically acceptable salt thereof is present in an amount from about 60% to about 90% by weight of the formulation.

14. The tranexamic acid tablet formulation of claim 1, wherein the tranexamic acid or pharmaceutically acceptable salt thereof is present in an amount from about 60% to about 80% by weight of the formulation.

15. The tranexamic acid tablet formulation of claim 1, wherein the modified release material is present in an amount from about 10% to about 35% by weight of the formulation.

16. The tranexamic acid tablet formulation of claim 1, wherein:
the tranexamic acid or pharmaceutically acceptable salt thereof is present in an amount from about 60% to about 90% by weight of the formulation;
the formulation is in the form of a matrix tablet which comprises a granulated drug mixed together with the modified release material and
the formulation provides a dose of about 650 mg of tranexamic acid per tablet.

17. The tranexamic acid tablet formulation of claim 16, wherein the tranexamic acid or pharmaceutically acceptable salt thereof is tranexamic acid.

18. The tranexamic acid tablet formulation of claim 16, wherein the modified release material comprises hydroxypropylmethylcellulose.

19. The tranexamic acid tablet formulation of claim 18, wherein the tranexamic acid or pharmaceutically acceptable salt thereof is tranexamic acid.

20. An oral dosage form comprising a tranexamic acid tablet formulation according to claim 1 coated with a film.

21. The oral dosage form of claim 20, wherein the film comprises a film-forming agent present in an amount in the range from about 2% tablet weight to about 4% tablet weight.

22. The oral dosage form of claim 20, wherein the film comprises a film-forming agent forming agent that comprises a (diethylaminoethyl) methacrylate/methyl-butyl-methacrylate copolymer.

23. The oral dosage form of claim 22, wherein the film forming agent comprises Eudragit E.

24. The oral dosage form of claim 20, wherein the tranexamic acid or pharmaceutically acceptable salt thereof is tranexamic acid.

25. The oral dosage form of claim 20, wherein the formulation provides a dose of about 650 mg of tranexamic acid per tablet.

26. The oral dosage form of claim 25, wherein the tranexamic acid or pharmaceutically acceptable salt thereof is tranexamic acid.

27. The oral dosage form of claim 20, wherein the modified release material comprises hydroxypropylmethylcellulose.

28. The oral dosage form of claim 27, wherein the formulation provides a dose of about 650 mg of tranexamic acid per tablet.

29. The oral dosage form of claim 28, wherein the tranexamic acid or pharmaceutically acceptable salt thereof is tranexamic acid.

30. The oral dosage form of claim 20, wherein the formulation is in the form of a matrix tablet which comprises a drug mixed together with a granulated modified release material.

31. The oral dosage form of claim 30, wherein the formulation provides a dose of about 650 mg of tranexamic acid per tablet.

32. The oral dosage form of claim 31, wherein the tranexamic acid or pharmaceutically acceptable salt thereof is tranexamic acid.

33. The oral dosage form of claim 20, wherein the tranexamic acid or pharmaceutically acceptable salt thereof is present in an amount from about 60% to about 90% by weight of the formulation.

34. The oral dosage form of claim 20, wherein the tranexamic acid or pharmaceutically acceptable salt thereof is present in an amount from about 60% to about 80% by weight of the formulation.

35. The oral dosage form of claim 20, wherein the modified release material is present in an amount from about 10% to about 35% by weight of the formulation.

36. The oral dosage form of claim 20, wherein:
the tranexamic acid or pharmaceutically acceptable salt thereof is present in an amount from about 60% to about 90% by weight of the formulation;
the formulation is in the form of a matrix tablet which comprises a granulated drug mixed together with the modified release material and
the formulation provides a dose of about 650 mg of tranexamic acid per tablet.

37. The oral dosage form of claim 36, wherein the tranexamic acid or pharmaceutically acceptable salt thereof is tranexamic acid.

38. The oral dosage form of claim 36, wherein the modified release material comprises hydroxypropylmethylcellulose.

39. The oral dosage form of claim 38, wherein the tranexamic acid or pharmaceutically acceptable salt thereof is tranexamic acid.

40. A method of treating menorrhagia comprising administering to a patient in need of such treatment at least one tablet of the tranexamic acid formulation of claim 1, wherein the formulation provides a dose of about 650 mg of tranexamic acid per tablet.

41. A method of treating menorrhagia comprising administering to a patient in need of such treatment at least one oral dosage form according to claim 20, wherein the oral dosage form provides a dose of about 650 mg of tranexamic acid.

* * * * *